US011040271B1

(12) United States Patent
Sines

(10) Patent No.: US 11,040,271 B1
(45) Date of Patent: Jun. 22, 2021

(54) CARD INTERMIXING DEVICE

(71) Applicant: FreeFall LLC, Henderson, NV (US)

(72) Inventor: Randy D. Sines, Tucson, AZ (US)

(*) Notice: Subject to any disclaimer, the term of this patent is extended or adjusted under 35 U.S.C. 154(b) by 0 days.

(21) Appl. No.: 17/019,237

(22) Filed: Sep. 12, 2020

(51) Int. Cl.
*A63F 1/12* (2006.01)
*A61L 2/20* (2006.01)
*A61L 2/26* (2006.01)
*A61L 2/10* (2006.01)
*A61L 2/08* (2006.01)

(52) U.S. Cl.
CPC ............... *A63F 1/12* (2013.01); *A61L 2/085* (2013.01); *A61L 2/10* (2013.01); *A61L 2/202* (2013.01); *A61L 2/26* (2013.01)

(58) Field of Classification Search
CPC ... A63F 1/12; A61L 2/085; A61L 2/10; A61L 2/202; A61L 2/26
See application file for complete search history.

(56) References Cited

U.S. PATENT DOCUMENTS

| 4,807,884 A | 2/1989 | Breeding |
| 5,261,667 A | 11/1993 | Breeding |
| 5,303,921 A | 5/1994 | Breeding |
| 5,575,475 A | 11/1996 | Steinbach |
| 5,695,189 A | 12/1997 | Breeding et al. |
| 6,068,258 A | 5/2000 | Breeding et al. |
| 6,139,014 A | 10/2000 | Breeding et al. |
| 6,149,154 A * | 11/2000 | Grauzer ............... A63F 1/12 273/149 R |
| 6,250,632 B1 | 6/2001 | Albrecht |
| 6,325,373 B1 | 12/2001 | Breeding et al. |
| 6,568,678 B2 | 5/2003 | Breeding et al. |
| 6,651,981 B2 | 11/2003 | Grauzer et al. |
| 6,651,982 B2 | 11/2003 | Grauzer et al. |
| 7,036,818 B2 | 5/2006 | Grauzer et al. |
| 7,384,044 B2 | 6/2008 | Grauzer et al. |
| 7,523,935 B2 | 4/2009 | Grauzer et al. |
| 7,584,962 B2 | 9/2009 | Breeding et al. |
| 7,998,152 B2 | 8/2011 | Sines |
| 8,408,551 B2 | 5/2013 | Soltys |
| 8,469,360 B2 | 7/2013 | Sines |
| 8,720,892 B2 | 5/2014 | Sines |
| 8,967,621 B2 | 3/2015 | Sines et al. |

(Continued)

*Primary Examiner* — Sean E Conley
(74) *Attorney, Agent, or Firm* — Eugene Vamos

(57) ABSTRACT

A device and methods for intermixing playing cards in a card stack used in casino gaming. The device includes a card-edge lifting structure for lifting the edges of adjacent sub-stacks of playing cards and two push surfaces which translate the sub-stacks closer. When the cards from the adjacent sub-stacks slip past the shaft of the card-edge lifting structure, the cards fall and interleave. The cards are "squared up" and repositioned, completing the card intermixing cycle. The card stack goes through a plurality of card intermixing cycles to obtain the necessary card randomness. Because the card falling is only being acted upon by gravity, the device is simple and compact. A number of embodiments that change the card falling characteristics and the randomness of the card stack are described. A card funnel is further described that allows a card stack to be "squared up" prior to the card intermixing process, minimizing the misalignment of the card stack and potential failures in the card intermixing process.

12 Claims, 19 Drawing Sheets

(56) References Cited

U.S. PATENT DOCUMENTS

| | | |
|---|---|---|
| 9,233,298 B2 | 1/2016 | Sines |
| 9,504,905 B2 | 11/2016 | Kelley et al. |
| 9,539,494 B2 | 1/2017 | Sines et al. |
| 9,901,810 B2 | 2/2018 | Rynda |

* cited by examiner

US 11,040,271 B1

CARD INTERMIXING DEVICE

CROSS-REFERENCE TO RELATED APPLICATIONS

Not Applicable

STATEMENT REGARDING FEDERALLY SPONSORED RESEARCH/DEVELOPMENT

Not Applicable

THE NAMES OF THE PARTIES TO A JOINT RESEARCH AGREEMENT

Not Applicable

REFERENCE TO A "SEQUENCE LISTING," A TABLE, OR A COMPUTER PROGRAM

Not Applicable

STATEMENT REGARDING PRIOR DISCLOSURES BY AN INVENTOR OR JOINT INVENTOR

Not Applicable

BACKGROUND OF THE INVENTION

Field of Invention

The Card Intermixing Device generally relates to the field of card intermixing for applications in the casino gaming industry.

Historical Synopsis of Casino Shufflers

In the mid/late 1980's the casino industry began experimenting with shuffling machines in an effort to increase productivity and game security. Peripheral Dynamics Inc. introduced one of the first models, which featured two discard bins built into the back of a dealing shoe where the cards could be discarded, alternately. The cards in each bin were combined at the bottom by directing 1-3 cards from each side in riffle-shuffle fashion. After these cards were shuffled, they worked their way to the front of the shoe ready to be dealt. This process created the first of the "continuous shuffles."

Shuffle Master Inc. was the first company to offer a fully automated single-deck shuffler. Their first shuffler split the deck into two halves and used a steel ball to raise the corners of the halves forcing a riffle, which was then repeated a number of cycles. This automated single-deck shuffler went through three generations (BG-1, BG-2, and BG-3) before being replaced by their random-position shufflers. Shuffle Masters's first multi-deck shuffler is known as the MD Shuffler. The MD Shuffler is now in its third generation (MD3) and is currently the most popular multi-deck shuffler in the world today. The MD Shuffler employs a roller-based system to first split the decks into two piles (one card at a time), and then to combine the two halves into a center, common bin (one card at a time). A "batch system" is used with both shufflers (two decks or two sets of decks are used in rotation). ProShuffle is another model that emulates the riffle shuffle, though it requires the dealer to manually split the deck before emulating the riffle. It shuffles one to six decks.

In 2005, Shuffle Tech introduced its shuffler as the "world's first fully automatic shuffler for home games." The shuffler can automatically divide the deck for a riffle and perform a 40-second casino shuffle with three riffles and one strip, or a "full randomization shuffle" in 120 seconds with seven riffles and one strip.

New shufflers are still introduced from time to time, for example, the New Shuffle King II, a shuffler from Europe. It is very similar to all riffle-based shufflers with the exception of starting the shuffle by first dividing the deck into ten packets before combining them with rollers. To summarize, the first true rifflers to actually perform a riffle were the simple mechanical rifflers of the 1940's. By 1987, the only true casino rifflers were Shuffle Masters's BG series. All other riffle-based shufflers would be better classified as "pseudo-rifflers" since there is no riffling action to combine the halves, but a roller-based action that moves cards one at a time from the halves to a common bin to build the shuffled deck.

The world of shuffling machines all changed in 2000 when Casinovations Inc. developed the Random Ejection Shuffler, the first casino non-riffle shuffler. This shuffler's random number generator selected a position from 1-312 in a six-deck game, and then 1-311, 1-310, 1-309, etc., each time moving an ejector to the selected position and ejected the selected card to the shuffled stack until the shuffle was complete.

Today, casino shufflers are classified according to the following four categories:

"Roller-Based" pseudo-rifflers (e.g., MD3 from Shuffle Master).

"Random-Selection" shufflers that can shuffle/move any selected card to the shuffled stack (e.g., Random Ejection Shuffler).

"Random-Position" shufflers feed cards off the top or bottom of the unshuffled stack into randomly selected shelves, bins, or positions before combining the cards into a shuffled stack (e.g., Savant Shuffler).

"Continuous" shufflers where the discarded cards are fed back into the shuffler to provide a never-ending or continuous supply of cards.

Historical Summary of Riffler Types
1906-1950's Early hand-cranked rifflers
1940's Mechanical rifflers
1950's-present Battery operated rifflers
1985 Roller-driven riffler built into dealing shoe—Peripheral Dynamics Inc.
1987 First true casino riffler—Shuffle Master's BG Series
1950's-present Automated and semi-automated roller-based rifflers
1997-present Shuffle Masters's MD Series The early history of shuffling machines is firmly based on the riffle shuffle. Shuffle Masters's first riffler (BG series)—has long been replaced by random-positioning shufflers, while ProShuffle, Shuffle Tech, and similar models have been limited to the private market. Shuffle Master's multi-deck shuffler (MD3) is the only casino shuffler still emulating the riffle shuffle (pseudo-riffler).

Technical Problems

Shuffling machines, or shufflers, are widely used in casinos, card rooms and many other venues at which card games are played. Conventional shufflers are typically adapted to receive one or more decks of standard playing cards to be shuffled. The intended purpose of most shufflers is to shuffle the playing cards into what is believed to be a random order. Such a random order of the playing cards is desirable and necessary when playing various types of card games such as blackjack, poker, baccarat and the like. However, in reality many shufflers have biases which can be exploited by a skilled player. Thus, there is still a need for automated shufflers that function in a manner which better randomizes the ordering of a deck or decks of playing cards.

Other problems associated with conventional shufflers, particularly multi-deck models, include excessive size, excessive weight, excessive mechanical complexity, excessive shuffle time and/or electrical complexity. These excessive complexities yield an inordinate amount of failures, commonly known as "jams". This generally results in shutting down the gaming table and calling in a technical person to repair the problem. Substantial frustration and lost revenues are generated to both the house and the players whom are often begrudgingly moved to another table.

Solution Approaches

A fifth riffler category has emerged in the field of casino shufflers with the development of the card intermixing device (90), which will be known commercially as the FreeFall gravity drop shuffler. Single or multiple decks of cards "freely" fall into an interleaved card stack, unlike true (non-pseudo) riffler based shufflers which utilize elastic energy and are not capable of nor been used to shuffle large stacks of multiple decks.

By having cards fall solely being acted upon gravity, the card intermixing device (90) described herein can accommodate from one up to ten or more decks for a random shuffle with only 50-70 mechanical movements with no direct individual card movements, as compared to the current shufflers being used in the gaming industry today that utilize an estimated 4,000 to 5,000 individual card movements during a 6-deck "pseudo" riffle shuffle. The design complexity of these current shufflers make for continual jams with high downtime cost for the casino industry; such reliability issues are solved by the elegant card intermixing device (90) design.

For example, the Shuffle Master multi-deck shuffler (MD3) needs to perform approximately 4,300 independent mechanical movements (as a minimum) in each shuffle for their 6-deck shuffler. These movements are primarily made by rollers moving each card a large number of times to just "simulate" a riffle shuffle (pseudo-riffle) and do it for several cycles for each shuffle. The Shuffle Master multi-deck shuffler (MD3) moves the shuffled cards almost ⅙ of a mile or almost three football fields in just one shuffle. Of course the MD3 is wrought with costly and excessive card jams, often once a shift.

The current trend in shuffler design is moving towards a non-riffle concept, as many experts consider the riffle concept to be outdated. The riffle design concept potential within the context of an automatic casino shuffling machine has never been realized until the FreeFall Shuffler.

BRIEF SUMMARY OF THE INVENTION

The card intermixing device (90) allows cards (600) in a card stack (605) to be intermixed as to change the relative positions of the cards (600) within the card stack (605) through a "card intermixing process". The intermixing of cards (600) randomizes the positioning of the cards (600) within the card stack (605) relative to the initial positioning of the cards (600) within the card stack (605). The card stack (605) may vary from a single deck to ten or more decks.

The card stack (605) is cut into a first sub-stack (610) and a second sub-stack (620). A card-edge lifting structure (500) rises and lifts the card-edges of the first sub-stack (610) and the card-edges of the second sub-stack (620). Once the card-edge lifting structure (500) reaches a certain height, the cards (600) of the first sub-stack (610) and cards (600) of the second sub-stack (620) begin to fall by being acted upon gravity. As the card-edge lifting structure (500) continues to rise, the remaining cards (600) of the first sub-stack (610) and the second sub-stack (620) fall by being acted upon gravity.

As they fall by being acted upon gravity, the cards (600) of the first sub-stack (610) and the second sub-stack (620) interleave. The number of cards (600) that fall together at a time is a random phenomenon, ranging from one to approximately ten cards, allowing for a randomized intermixing. This randomized intermixing prevents a perfect one by one interleaving, obviating concerns of a faro shuffle. The number of cards (600) that fall together at a time follows a probability distribution. The shape of this probability distribution is dependent on the design of the card intermixing device (90) and the specific movements of the elements of the card intermixing device (90). FIG. 19 illustrates various example probability distributions for the number of cards (600) that fall together at a time.

Once all the cards (600) from the first sub-stack (610) and the second sub-stack (620) have fallen and become interleaved, the cards (600) are "squared up" into the card stack (605) and the card stack (605) is repositioned for the next step: either a) the intermixing of the cards (600) is completed and the card stack (605) is lifted out of the housing (800) orb) the intermixing of the cards (600) continues and the card stack (605) is cycled again through the card intermixing process.

The card intermixing device (90) is configured to intermix the cards (600) of the card stack (605) repeatedly and automatically. The number of interleaving cycles that the card stack (605) goes through is pre-determined to ensure an adequately randomized card stack (605).

BRIEF DESCRIPTION OF THE SEVERAL VIEWS OF THE DRAWING

FIGS. 12 (A)-(D) show a front view of the card-edge lifting structure (500) comprising a shaft (520), a card separator wall (510), and a pivot connection (540).

DETAILED DESCRIPTION OF THE INVENTION

General Parts

Figure 1:
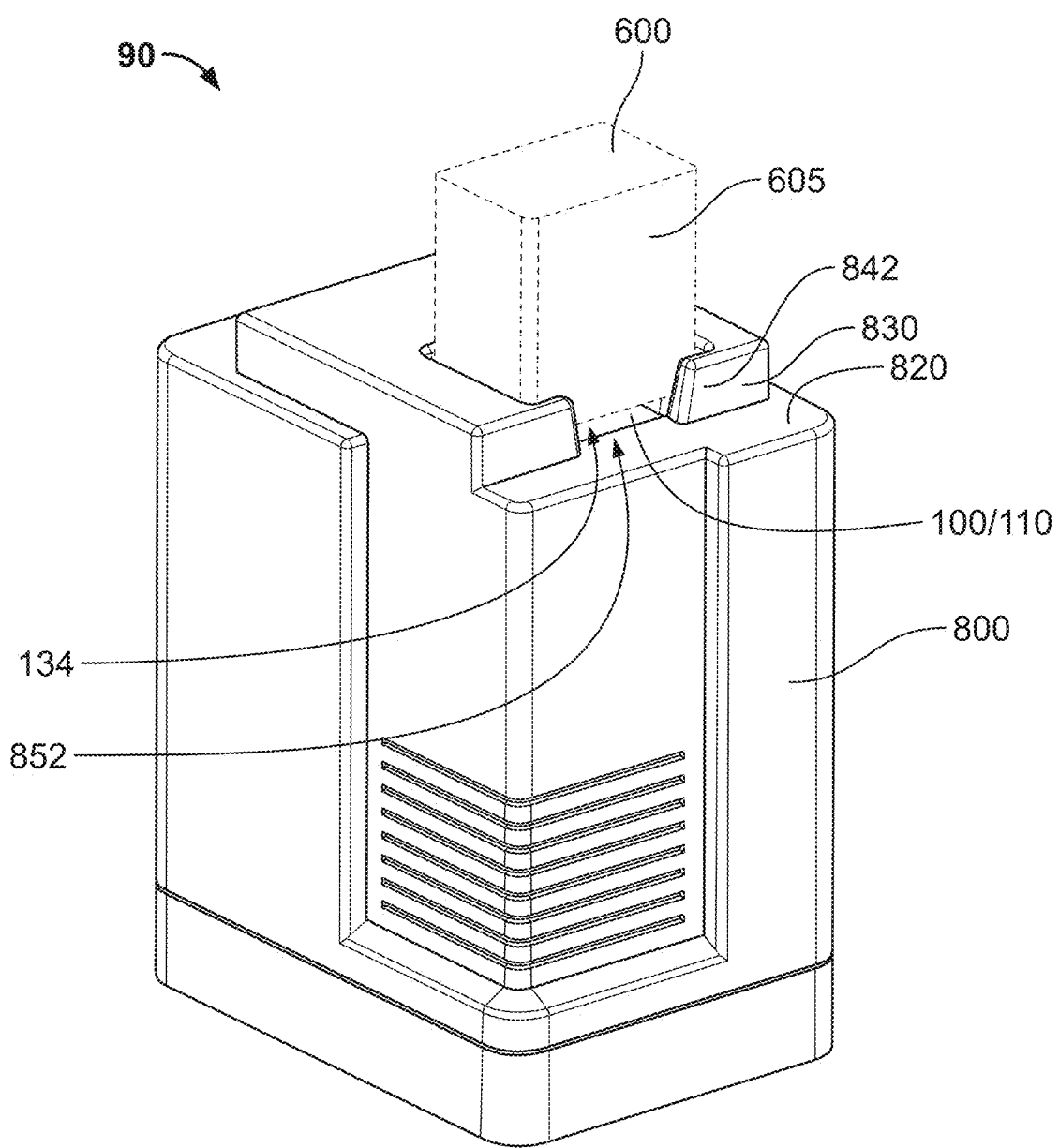
FIG. 1 shows a perspective view of the housing (800) of the card intermixing device (90), with a card stack (605) placed through the card funnel (830) onto the first card-receiving surface (110) of the first card-receiving structure (100).

The card intermixing device (90) comprises a first card-receiving structure (100), a second card-receiving structure (200), a first push surface (300), a second push surface (400), a card-edge lifting structure (500), a housing (800), a means to linearly translate the first push surface (920), and a means to linearly translate the second push surface (930). The card intermixing device (90) may further comprise a means to sanitize cards (700).

Housing (800)

The housing (800) provides a physical barrier to the elements of the card intermixing device (90) housed within the housing (800), preventing tampering of these elements. The housing (800) also provides a physical barrier to the cards (600) being intermixed, preventing tampering of the cards (600) during the intermixing process.

A card stack (605) is placed onto the first card-receiving surface (110) through the top surface (820) of the housing (800) (top-loading housing embodiment) or the side surface (860) of the housing (800) (side-loading housing embodiment).

Top-loading Housing Embodiment

Figure 4:
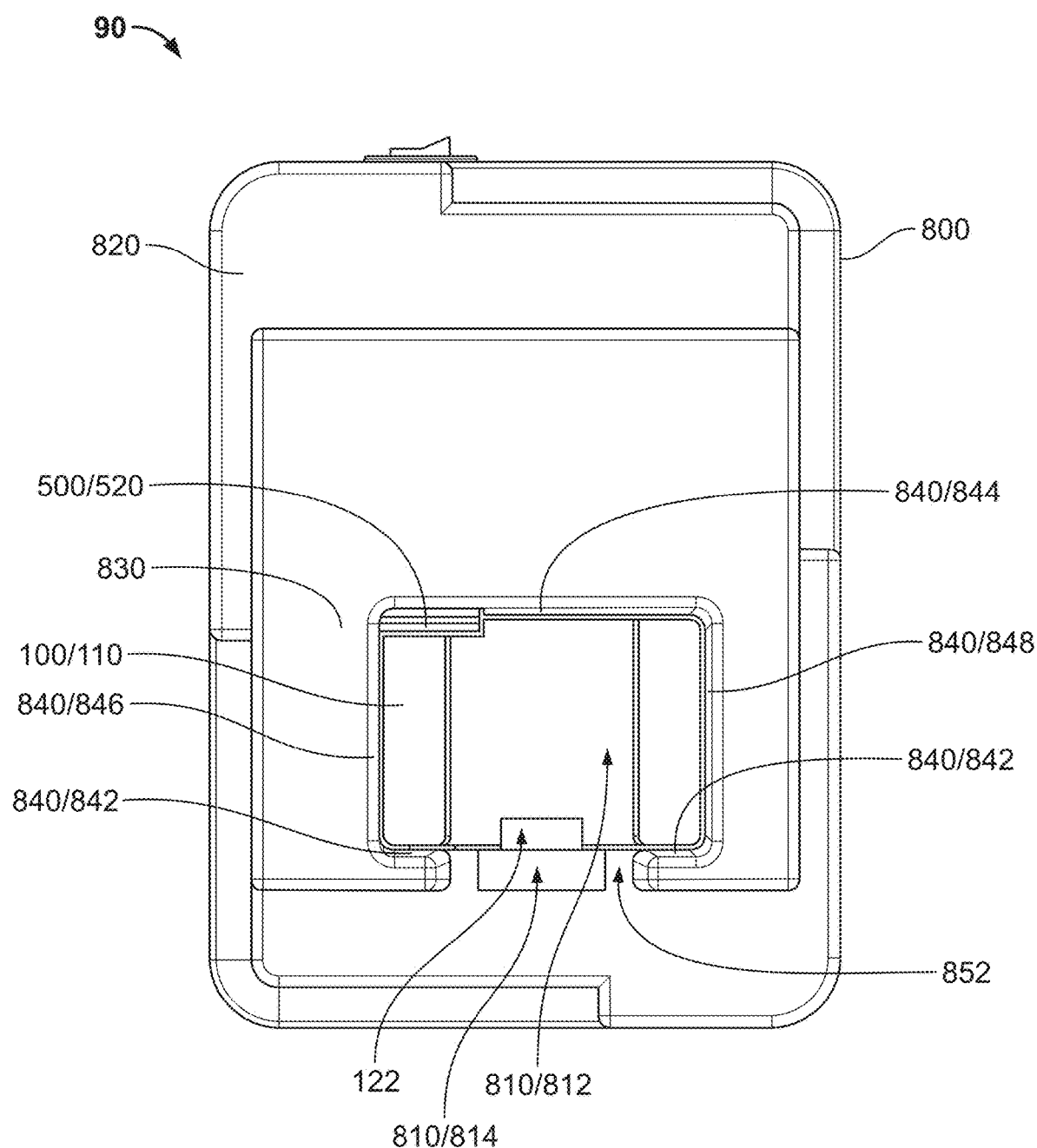
FIG. 4 shows a top view of the housing (800) of the card intermixing device (90), where a card funnel (830) is connected to the top surface (820) of the housing (800). The card funnel (830) has four side surfaces (840): a first side surface (842), a second side surface (844), a third side surface (846), and a fourth side surface (848).

The housing comprises a top surface (820). The top surface (820) comprises a top aperture (810). The top aperture (810) allows the card stack (605) to be moved in and out of the housing (800). The top aperture (810) is rectangular and sized to fit a standard playing card (600). Alternatively, the top aperture (810) may be formed by two shapes: a first shape (812) and a second shape (814). The first shape (812) is rectangular and sized to fit a standard playing card (600). The second shape (814) lies to the side of the first shape (812) and allows the dealer better access to the bottom of the card stack (605) and the use of a thumb or fingers to load the card stack (605) or to remove the card stack (605) from the first card-receiving structure (100). FIG. 4 shows the top surface (820) with the top aperture (810), the top aperture (810) having a first shape (812) and a second shape (814).

The top surface (820) may further comprise a card funnel (830). The card funnel (830) surrounds the card stack (605) being placed onto the first card-receiving surface (110) prior to the card stack (605) being lowered through the top aperture (810). The card funnel (830) surrounds the card stack (605) after the card stack (605) emerges through the top aperture (810). FIG. 1 shows a perspective view of the housing (800) of the card intermixing device (90), with a card stack (605) placed through the card funnel (830) onto the first card-receiving surface (110) of the first card-receiving structure (100).

Depending on the number of cards (600) in the card stack (605) being placed onto the first card-receiving surface (110), the card funnel (830) surrounds a portion or all of the card stack (605). For example, when four to six deck card stack (605) is placed onto the first card-receiving surface (110), only a portion of the card stack (605) is surrounded by the card funnel (830). When a one deck card stack (605) is placed onto the first card-receiving surface (110), the entire card stack (605) is surrounded by the card funnel (830).

The card funnel (830) is shaped as a pyramid frustrum. The card funnel (830) comprises a top opening (832), a bottom opening (834), and three or more side surfaces (840). The top opening (832) is larger than the bottom opening (834) so that the cross section of the card funnel (830) decreases as a function of the height of the card funnel (830) and the side surfaces (840) of the card funnel (830) taper inward. The inward tapering of the side surfaces (840) of the card funnel (830) repositions individual cards (600) relative to the card stack (605), "squaring up" the card stack (605) as the card stack (605) is lowered through the bottom opening (834) of the card funnel (830). The "squaring up" of the card stack (605) minimizes intermixing errors caused by incorrect card positioning. The card funnel (830) allows the dealer to stack the cards (600) within the card funnel (830) without having to manually "square up" the card stack (605). This allows the dealer to concentrate on other dealing actions.

Figure 2:
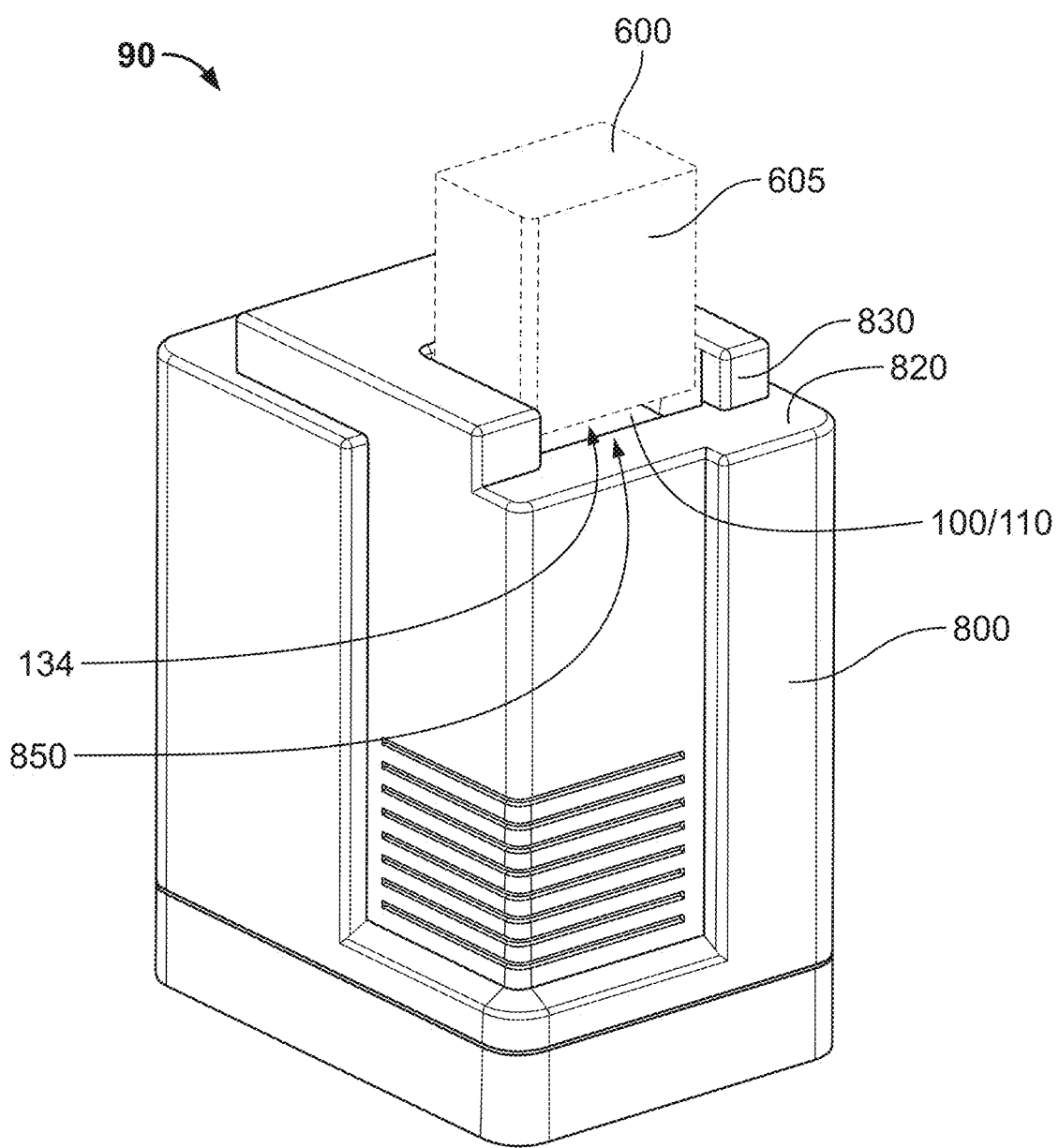
FIG. 2 shows a perspective view of the housing (800) of the card intermixing device (90), with a card stack (605) placed through the card funnel (830), where the card funnel (830) has a first side surface aperture (850).

In a first embodiment, the card funnel (830) comprises a top opening (832), a bottom opening (834), a second side surface (844), a third side surface (846), a fourth side surface (848) and an first side surface aperture (850) where the first side surface (842) would normally be located. The second side surface (844) is connected to the third side surface (846) and the fourth side surface (848). FIG. 2 shows a perspective view of the housing (800) of the card intermixing device (90), with a card stack (605) placed through the card funnel (830), where the card funnel (830) has a first side surface aperture (850).

In a second embodiment, the card funnel (830) comprises a top opening (832), a bottom opening (834), a first side surface (842), a second side surface (844), a third side surface (846), a fourth side surface (848), and a first side surface aperture (850). The first side surface aperture (850) is coplanar with the first side surface (842). The second side surface (844) is connected to the third side surface (846) and the fourth side surface (848). The first side surface (842) is connected to the third side surface (846) and the fourth side surface (848). The first side surface (842) has a first side surface notch (852). FIG. 4 shows a top view of the housing (800) of the card intermixing device (90), where a card funnel (830) is connected to the top surface (820) of the housing (800). The card funnel (830) has four side surfaces (840): a first side surface (842), a second side surface (844), a third side surface (846), and a fourth side surface (848). The first side surface (842) has a first side surface notch (852). FIG. 1 shows a card funnel (830) with a first side surface (842) with a first side surface notch (852).

Figure 5:
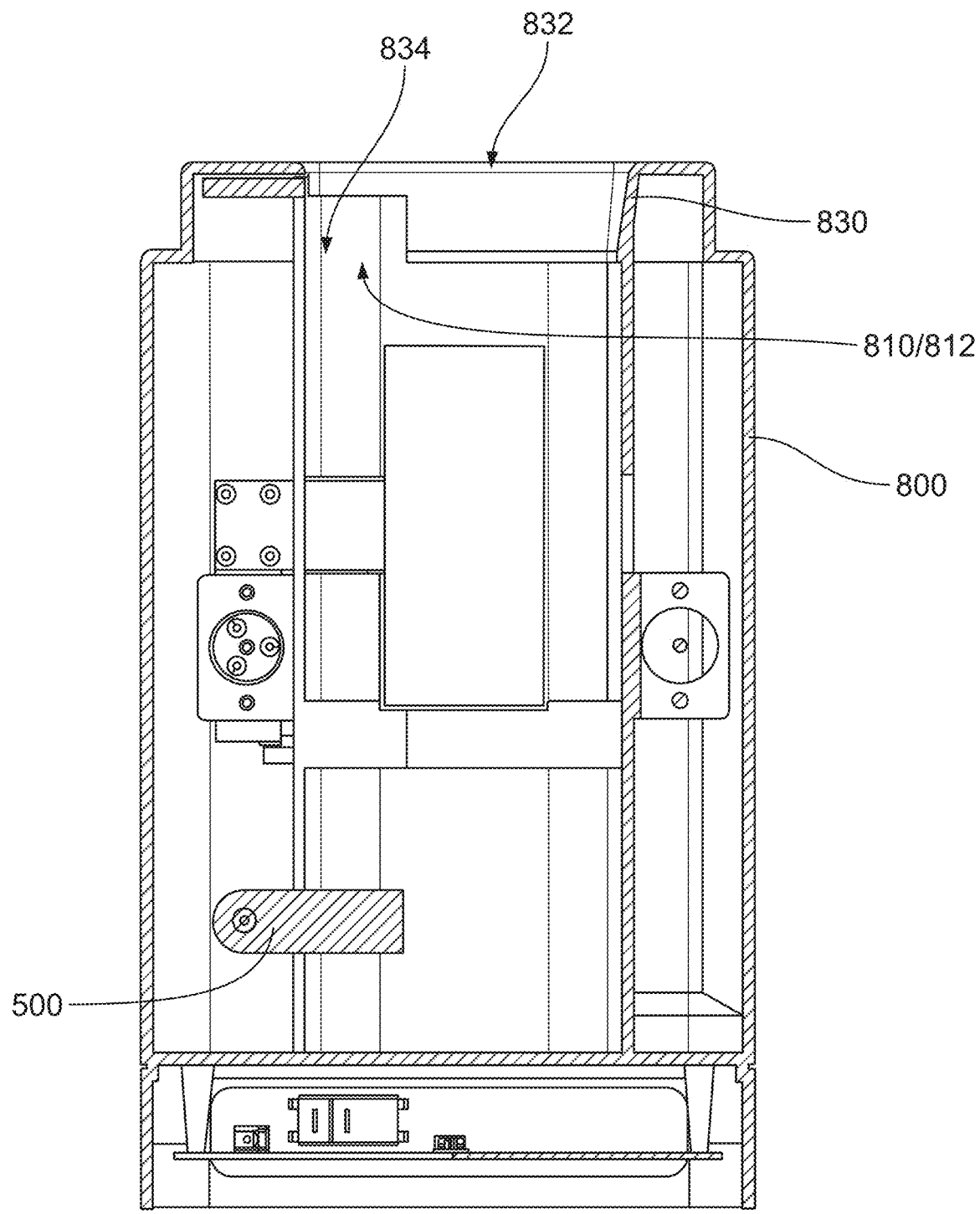
FIG. 5 shows a side sectional view of the housing (800), where the card funnel (830) has a top opening (832) and a bottom opening (834) and is connected to the top surface (820) of the housing (800). The top surface (820) has a top aperture (810). The bottom opening (834) of the card funnel (830) is positioned over the top aperture (810).

The bottom opening (834) of the card funnel (830) is positioned over the top aperture (810). When the top aperture (810) comprises a first shape (812) and a second shape (814), the second shape (814) is aligned with the fourth side of the card funnel (830). FIG. 5 shows a side sectional view of the housing (800), where the card funnel (830) has a top opening (832) and a bottom opening (834) and is connected to the top surface (820) of the housing (800). The top surface (820) has a top aperture (810). The bottom opening (834) of the card funnel (830) is positioned over the top aperture (810).

Figure 9:
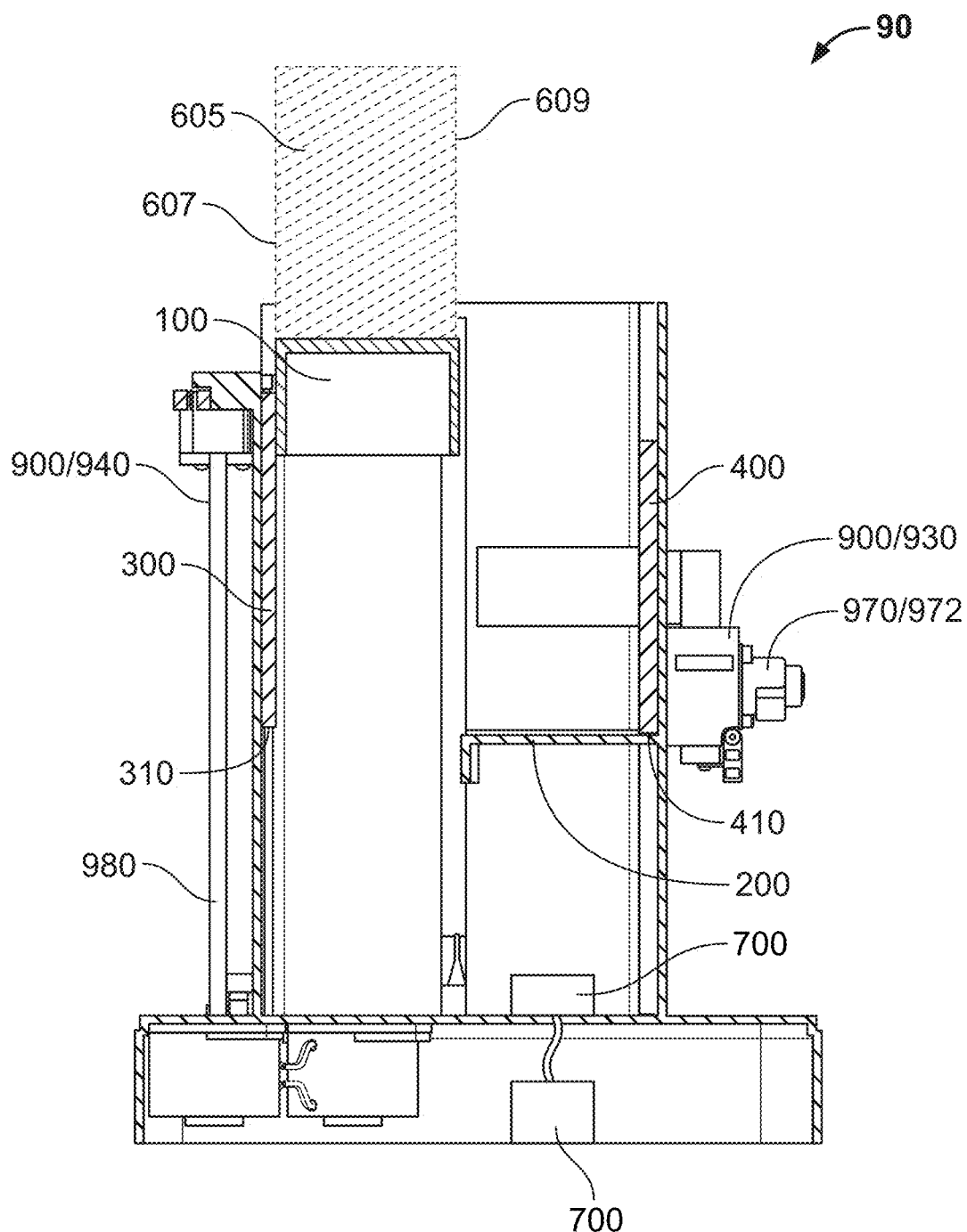
FIG. 9 shows a front sectional view of the housing (800), where the first card-receiving surface (110) is located adjacent to the top aperture (810) of the housing (800) and a card stack (605) has been placed onto the first card-receiving surface (110).

To start the card stack loading sequence, the first card-receiving surface (110) is vertically translated so that it can be accessed through the top aperture (810) of the top surface (820) or the side aperture (870) of the side surface (860), depending on the housing (800) embodiment being used. This allows the dealer to place the card stack (605) onto the first card-receiving surface (110). The first card-receiving surface (110) is translated by the means to linearly translate the first card-receiving surface (940). FIG. 9 shows a front sectional view of the housing (800), where the first card-receiving surface (110) is located adjacent to the top aperture (810) of the housing (800) and a card stack (605) has been placed onto the first card-receiving surface (110).

If the card funnel (830) is present, the dealer places the card stack (605) into the card funnel (830) through the top opening (832) or the first side surface aperture (850) of the card funnel (830). When the dealer finishes placing the card stack (605) onto the first card-receiving surface (110), the first card-receiving surface (110) is vertically translated downwards. As the first card-receiving surface (110) is lowered, the cards (600) in the card stack (605) are "squared up" by the tapering of the side surfaces (840) of the card funnel (830). By the time the entire card stack (605) has been lowered through the first shape (812) of the top aperture (810), the card stack (605) is "squared up" and is ready to be intermixed.

The card stack (605) is normally composed of cards (600) from one or more card decks, the choice of cards (600) comprising the card deck (605) depending on the type of casino game that is being played. For example, casino blackjack is most commonly played with six to eight decks of standard 52 playing cards, excluding jokers.

Side-Loading Embodiment

Figure 3:
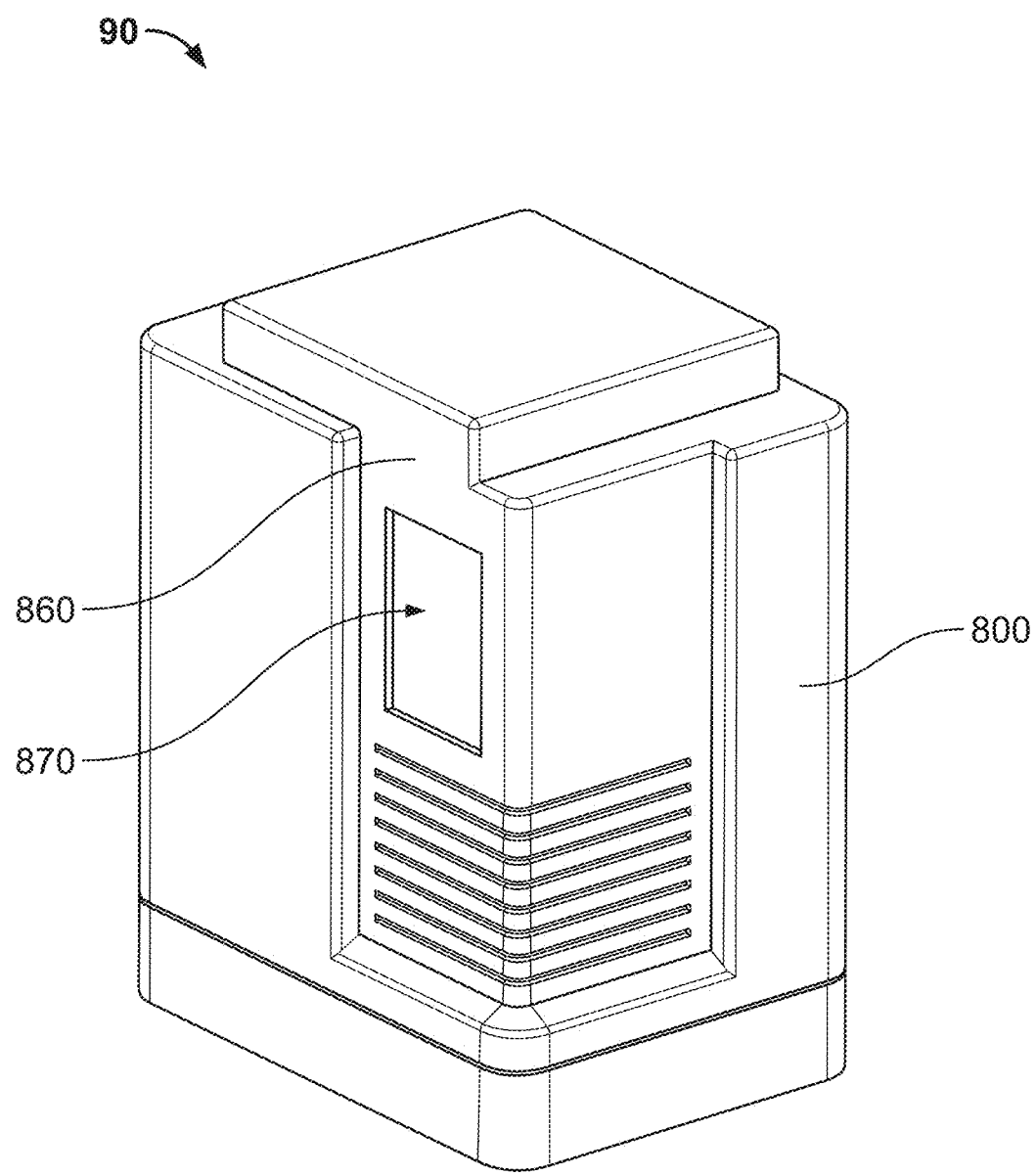
FIG. 3 shows a perspective view of the housing (800) of the card intermixing device (90), where the housing (800) has a side aperture (870).

The side-loading embodiment allows the dealer to insert the card stack (605) from a side of the housing (800) rather than the top of the housing (800). The housing (800) comprises a side surface (860). The side surface (860) comprises a side aperture (870). The side aperture (870) size may vary to accommodate a card stack (605) ranging from a single deck to ten or more decks. FIG. 3 shows a perspective view of the housing (800) of the card intermixing device (90), where the housing (800) has a side aperture (870).

To start the card stack loading sequence, the first card-receiving surface (110) is vertically translated so that it can be accessed through the side aperture (870) of the side surface (860). This allows the dealer to place the card stack (605) onto the first card-receiving surface (110). The first card-receiving surface (110) is translated by the means to linearly translate the first card-receiving surface (940). When the dealer has finished placing the card stack (605), the first card-receiving surface (110) may have to be vertically translated depending on the location of the side aperture (870) on the side surface (860).

Inside the Housing (800)

The card stack (605) is intermixed inside the housing (800). The card stack (605) is cut into a first sub-stack (610) and a second sub-stack (620). The first sub-stack (610) and a second sub-stack (620) are then interleaved. Once interleaved, the cards (600) from the first sub-stack (610) and the second sub-stack (620) are "squared up" into the card stack (605), that is, the cards (600) are fully positioned over each other and the edges of the cards (600) do not protrude from the card stack (605).

The first sub-stack (610) comprises a first edge (612) and a second edge (614). The second sub-stack (620) comprises a first edge (622) and a second edge (624).

The first card-receiving structure (100) vertically translates the card stack (605) to a position inside the housing (800) where the card stack (605) can be intermixed. The first card-receiving structure (100) comprises a first card-receiving surface (110) and a means to linearly translate the first card-receiving surface (940). The first card-receiving surface (110) comprises a first edge (112), a second edge (114), third edge (116) and a fourth edge (118). The means to linearly translate the first card-receiving surface (940) is connected to the first card-receiving surface (110).

The first card-receiving surface (110) may further comprise a channel (120). The channel (120) may be oriented from the first edge (112) of the first card-receiving surface (110) to the second edge (114) of the first card-receiving surface (110). Alternatively, the channel (120) may be oriented from the third edge (116) of the first card-receiving surface (110) to the fourth edge (118) of the first card-receiving surface (110). The channel (120) creates a space (134) when the card stack (605) is positioned onto the first card-receiving surface (110). This space (134) allows the dealer to place a finger or a thumb under the card stack (605) for easier loading onto the first card-receiving surface (110) and for easier removal from the first card-receiving surface (110). The cross section of the channel (120) may be shaped as a trapezoid, square, rectangle, U, or any state-of-the-art cross section channel shapes.

The first card-receiving surface (110) may further comprise a finger notch (122). The finger notch (122) may be located on the first edge (112), second edge (114), third edge (116), or the fourth edge (118) of the first card-receiving surface (110), depending on the housing embodiment being utilized. The finger notch (122) in combination with the second shape (814) of the top aperture (810) allows the dealer to place a finger or a thumb under the card stack (605) for easier loading onto the first card-receiving surface (110) and for easier removal from the first card-receiving surface (110) in the Top-loading Housing (800) Embodiment.

Figure 8:
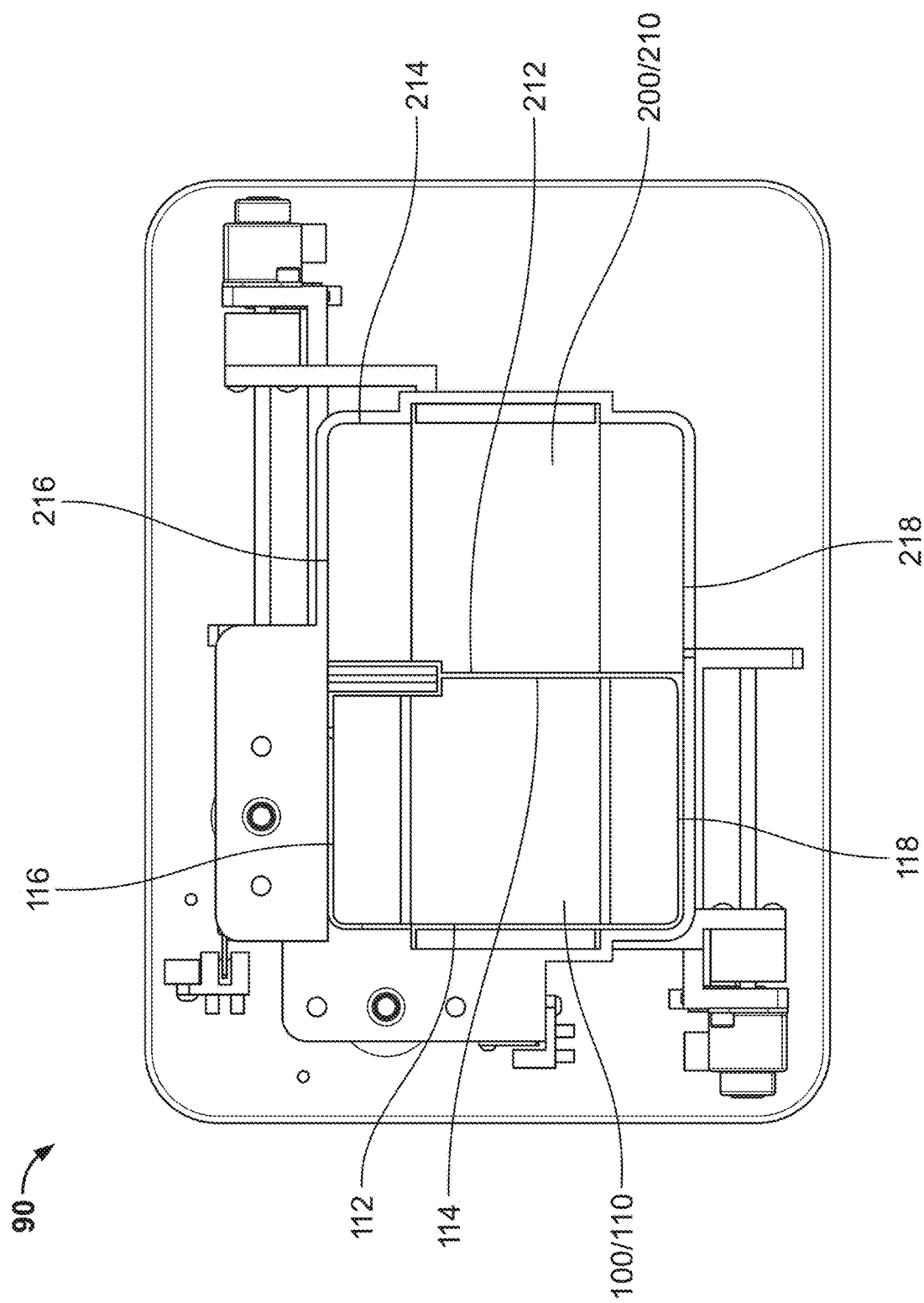
FIG. 8 shows a top sectional view of the housing (800), where the relative positioning of the first edge (112), second edge (114), third edge (116) and fourth edge (118) of the first card-receiving surface (110) is shown, and where the relative positioning of the first edge (212), second edge (214), third edge (216) and fourth edge (218) of the second card-receiving surface (210) is shown.

The second card-receiving structure (200) serves as a repository for the second sub-stack (620) that has been cut from the card stack (605). The second card-receiving structure (200) comprises a second card-receiving surface (210). The second card-receiving structure (200) may further comprise a means to linearly translate the second card-receiving surface. The second card-receiving surface (210) comprises a first edge (212), a second edge (214), a third edge (216) and a fourth edge (218). FIG. 8 shows a top sectional view of the housing (800), where the relative positioning of the first edge (112), second edge (114), third edge (116) and fourth edge (118) of the first card-receiving surface (110) is shown, and where the relative positioning of the first edge (212), second edge (214), third edge (216) and fourth edge (218) of the second card-receiving surface (210) is shown.

Figure 6:
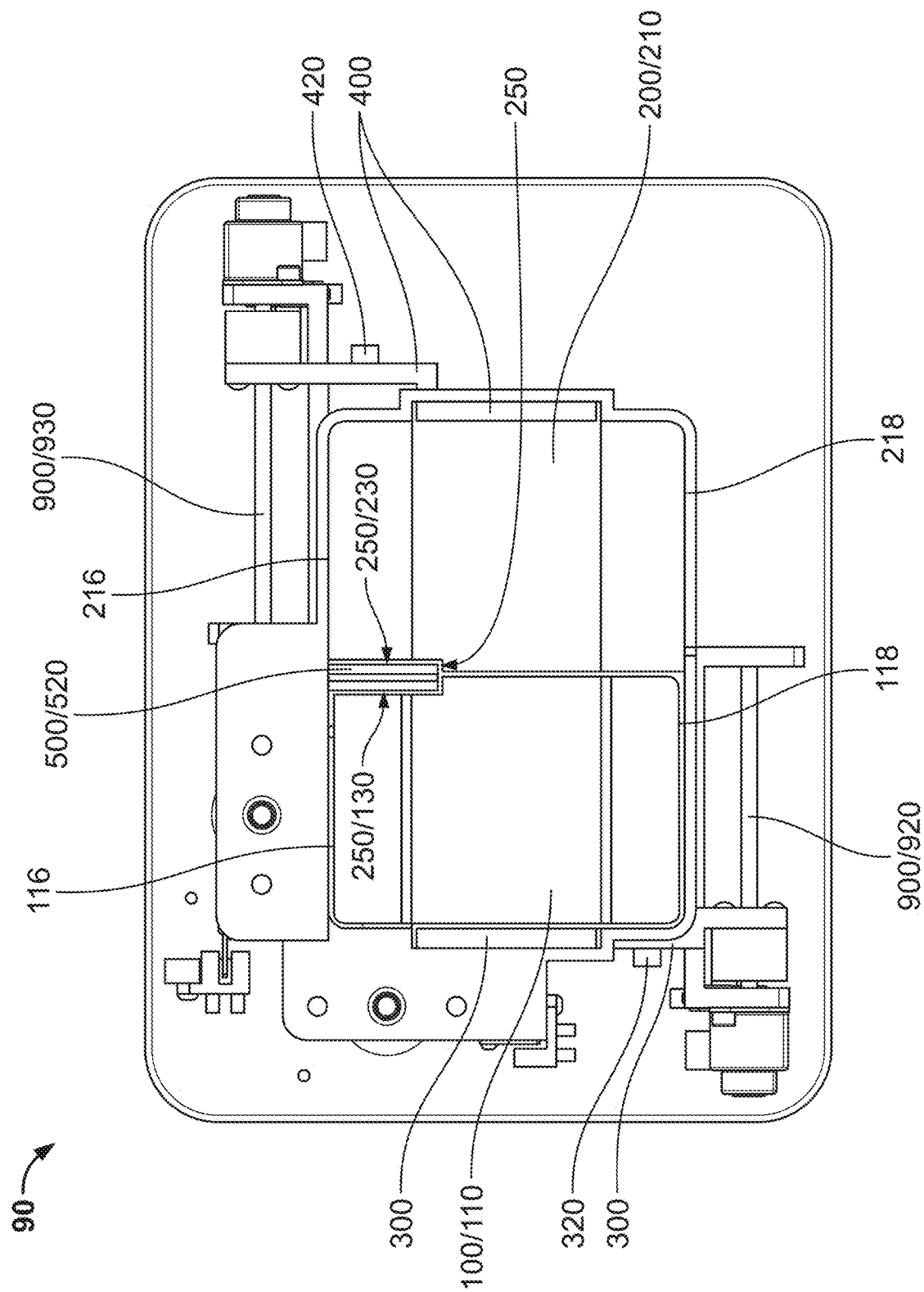
FIG. 6 shows a top sectional view of the housing (800), where the first card-receiving structure (100) is adjacent to the second card-receiving structure (200). A gap (250) is located between the first card-receiving surface (110) and the second card-receiving surface (210). The shaft (520) of the card-edge lifting structure (500) is positioned within the gap (250).

The first card-receiving structure (100) and the second card-receiving structure (200) are adjacent to each other, such that the second edge (114) of the first card-receiving surface (110) faces the first edge (212) of the second card-receiving surface (210) when viewed from the top of the card intermixing device (90). FIG. 6 shows a top sectional view of the housing (800), where the first card-receiving structure (100) is adjacent to the second card-receiving structure (200). A gap (250) is located between the first card-receiving surface (110) and the second card-receiving surface (210). The shaft (520) of the card-edge lifting structure (500) is positioned within the gap (250).

The means to linearly translate the second card-receiving surface allows the second card-receiving surface (210) to be vertically translated within the housing (800). This vertical translation allows the intermixing process to occur at different heights within the housing (800). For example, when an eight-ten deck card stack (605) is intermixed, the second card-receiving surface (210) may be vertically translated lower within the housing (800) so that the eight-ten deck card stack (605) can be accommodated. When a two-six deck card stack (605) is intermixed, the second card-receiving surface (210) may be vertically translated higher within the housing (800) so that the intermixing of the card stack (605) occurs higher within the housing (800). This allows the vertical translation of the first card-receiving surface (110) to be shorter in distance, reducing the travel time before and after the card stack (605) is intermixed, depending on the housing embodiment being utilized.

The first push surface (300) comprises a bottom edge (310). The first push surface (300) can translate some or all of the card stack (605). The first push surface (300) is initially positioned to the side of the first card-receiving surface (110), adjacent to the first edge (112) of first card-receiving surface (110) ("initial first push surface position"). The first push surface (300) serves at least two purposes: a) translates a portion of the card stack (605) from the first card-receiving structure (100) to the second card-receiving structure (200), and b) translates the first sub-stack (610) towards the second edge (114) of the first card-receiving surface (110) while the second edge (614) of first sub-stack (610) is being vertically translated upwards. The first push surface (300) is connected to the means to linearly translate the first push surface (920). The means to linearly translate the first push surface (920) translates the first push surface (300) towards the second edge (114) of the first card-receiving surface (110) and towards the first edge (112) of the first card-receiving surface (110).

The second push surface (400) comprises a bottom edge (410). The second push surface (400) can translate some or all of the card stack (605). The second push surface (400) is initially positioned to the side of the second card-receiving surface (210), adjacent to the second edge (214) of second card-receiving surface (210) ("initial second push surface position"). The second push surface (400) serves at least three purposes: a) provides a stop point for the portion of the card stack (605) being translated by the first push surface (300), b) translates the second sub-stack (620) towards the first edge (212) of the second card-receiving surface (210) while the first edge (612) of the second sub-stack (620) is being vertically translated up and c) translates the card stack (605) towards the first edge (112) of the first card-receiving surface (110). The second push surface (400) is connected to the means to linearly translate the second push surface (930). The means to linearly translate the second push surface (930) translates the second push surface (400) towards the first edge (212) of the second card-receiving surface (210) and towards the second edge (214) of the second card-receiving surface (210).

FIG. 6 shows a top sectional view of the housing (800), where the first push surface (300) is positioned to the side of the first card-receiving surface (110), and the second push surface (400) is positioned to the side of the second card-receiving surface (210).

Figure 13:
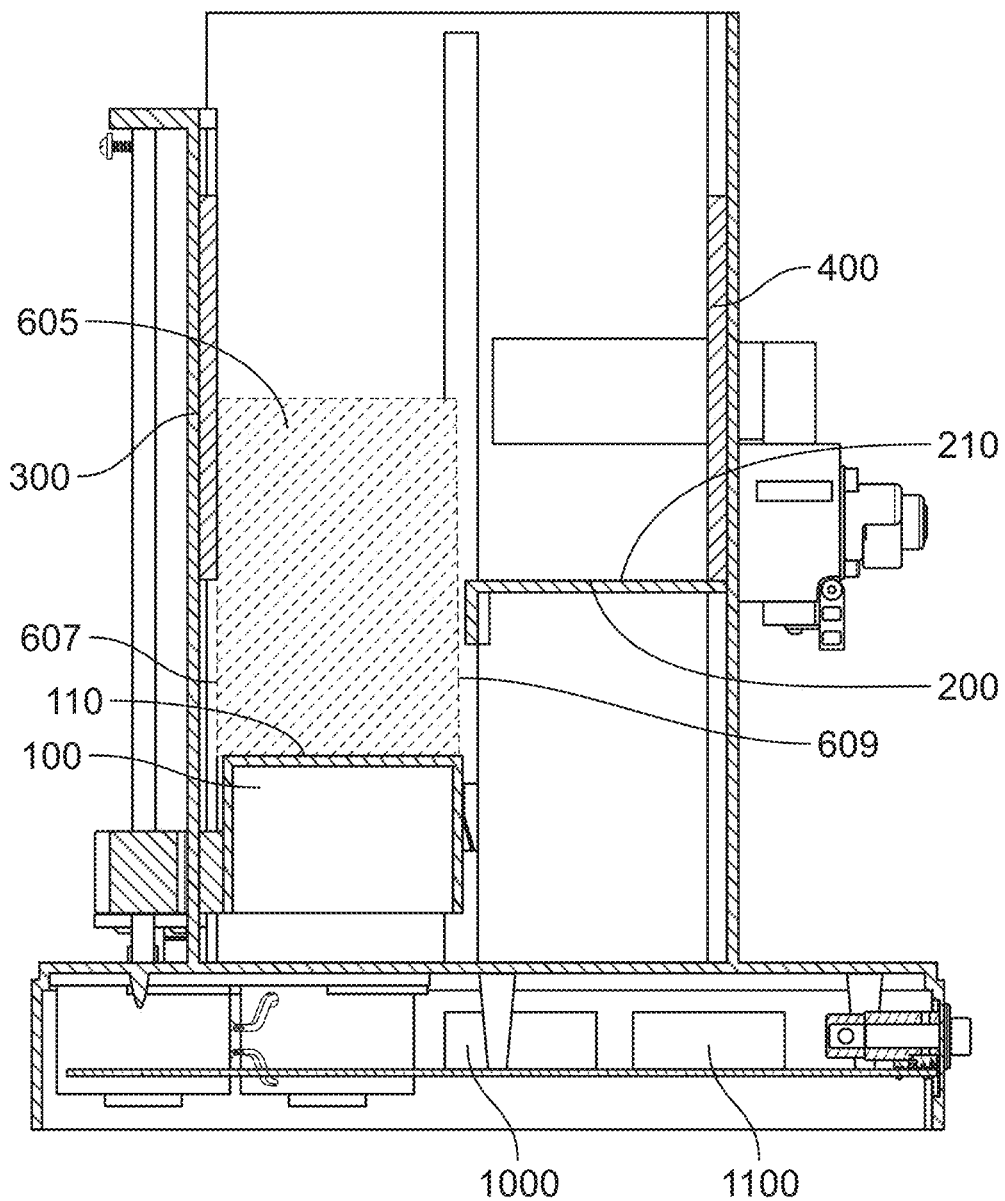
FIG. 13 shows a front sectional view of the housing (800), where the first card-receiving structure (100) has translated the card stack (605) so that a portion of the card stack (605) is aligned below the bottom edge (310) of the first push surface (300) (the first sub-stack (610)) and a portion of the card stack (605) is aligned above the bottom edge (310) of the first push surface (300) (the second sub-stack (620)).

To cut the card stack (605) into a first sub-stack (610) and a second sub-stack (620), the first push surface (300) is positioned in its initial first push surface position and the second push surface (400) is positioned in its initial second push surface position. The means to linearly translate the first card-receiving surface (940) translates vertically the first card-receiving surface (110) so that a portion of the card stack (605) is aligned below the bottom edge (310) of the first push surface (300) (the first sub-stack (610)) and a portion of the card stack (605) is aligned above the bottom edge (310) of the first push surface (300) (the second sub-stack (620)). When the first card-receiving surface (110) translates from the top aperture (810) of the housing (800), the first card-receiving surface (110) translates vertically downward. At this point, the first card-receiving surface (110) and the second card-receiving surface (210) are not necessarily flush. This "off-set" determines the height variation between the first sub-stack (610) and the second sub-stack (620) after being cut from the card stack (605). FIG. 13 shows a front sectional view of the housing (800), where the first card-receiving structure (100) has translated the card stack (605) so that a portion of the card stack (605) is aligned below the bottom edge (310) of the first push surface (300) (the first sub-stack (610)) and a portion of the card stack (605) is aligned above the bottom edge (310) of the first push surface (300) (the second sub-stack (620)).

Figure 14:
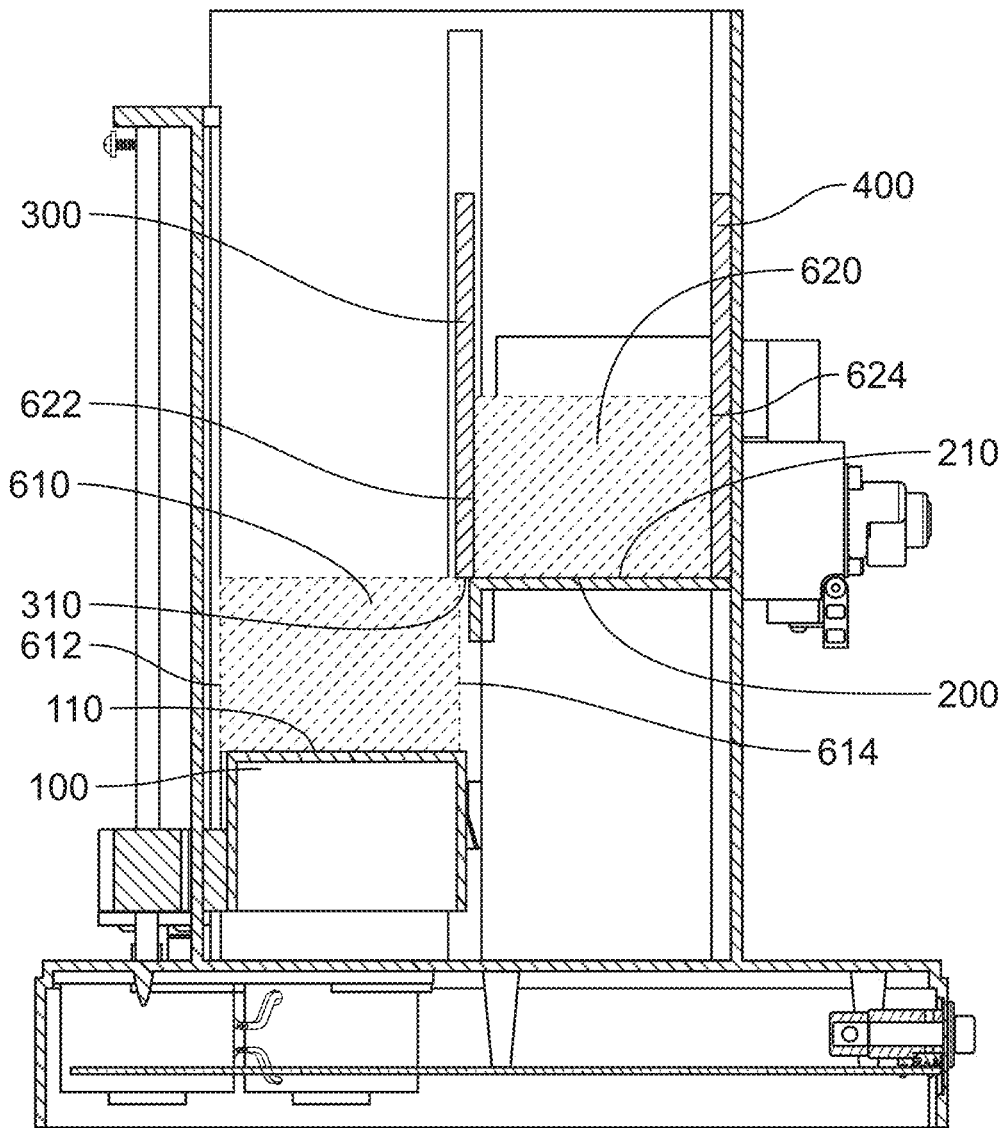
FIG. 14 shows a front sectional view of the housing (800), where the first push surface (300) has translated the second sub-stack (620) onto the second card-receiving surface (210).

The first push surface (300) then translates towards the second edge (114) of the first card-receiving surface (110), coming in contact with the portion of the card stack (605) aligned above the bottom edge (310) of the first push surface (300) (the second sub-stack (620)). The second sub-stack (620) is translated towards the second edge (214) of the second card-receiving surface (210) until it is positioned onto the second card-receiving surface (210). The second sub-stack (620) is now positioned adjacent to the first sub-stack (610). The second push surface (400) provides a stop point for the second sub-stack (620) and prevents further translation. The cards (600) in the card stack (605) below the bottom edge (310) of the first push surface (300) do not translate and remain over the first card-receiving surface (110)—the first sub-stack (610). FIG. 14 shows a front sectional view of the housing (800), where the first push surface (300) has translated the second sub-stack (620) onto the second card-receiving surface (210).

Figure 15:
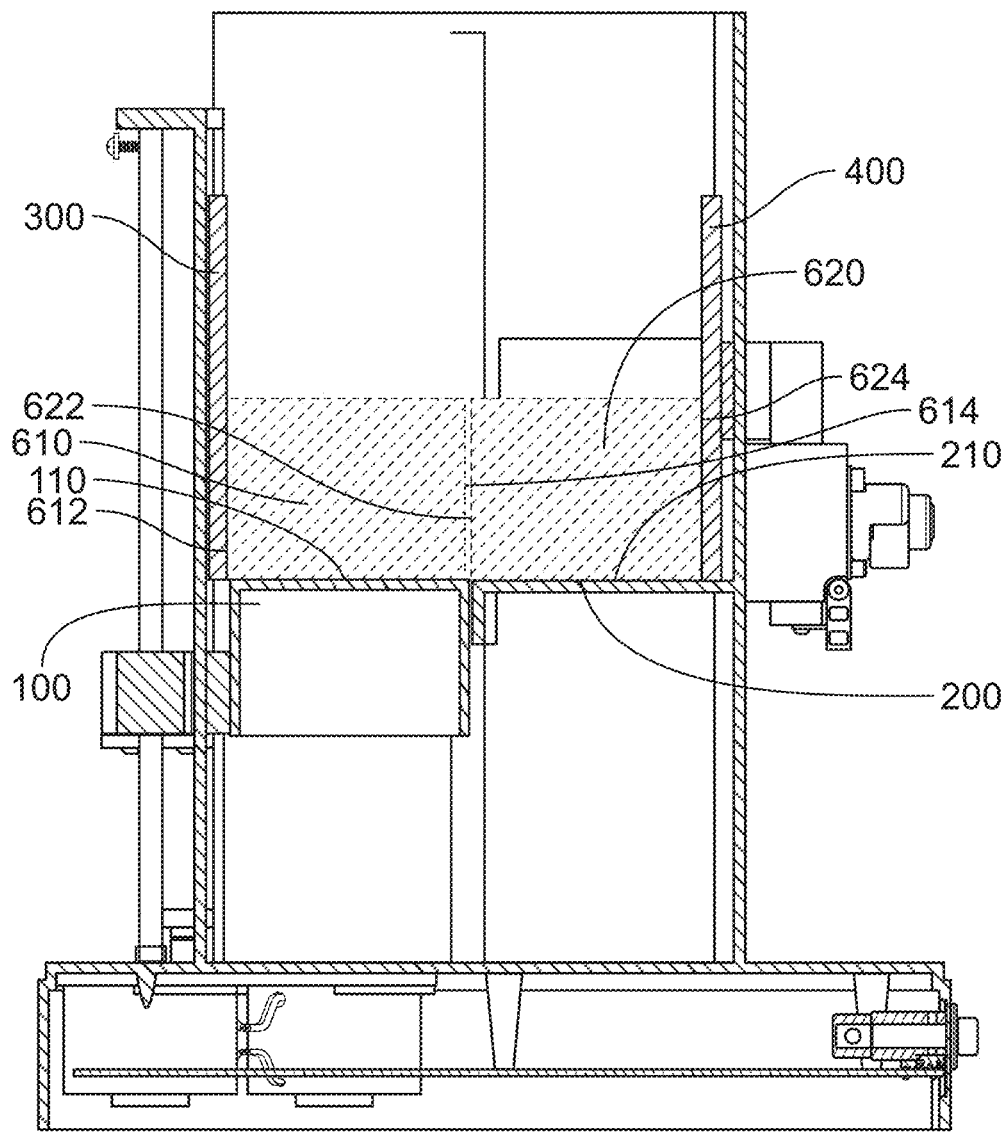
FIG. 15 shows a front sectional view of the housing (800), where the first card-receiving surface (110) is aligned to the second card-receiving surface (210) so that the first sub-stack (610) is adjacent to the second sub-stack (620).

Once the second sub-stack (620) is positioned onto the second card-receiving surface (210), the first push surface (300) returns to its initial first push surface position. The first card-receiving surface (110) is vertically translated upwards until the first card-receiving surface (110) and the second card-receiving surface (210) are substantially flush. This also means that the bottom (616) of the first sub-stack (610) and the bottom (626) of the second sub-stack (620) are substantially flush. FIG. 15 shows a front sectional view of the housing (800), where the first card-receiving surface (110) is aligned to the second card-receiving surface (210) so that the first sub-stack (610) is adjacent to the second sub-stack (620).

The means to linearly translate the first card-receiving surface (940) has the ability to position a variable portion of the card stack (605) below the bottom edge (310) of the first push surface (300). This allows for the card stack (605) to be cut at different heights, creating a height variation between the first sub-stack (610) and the second sub-stack (620). This provides another way to increase randomness, by varying the cut height in each cycle of card intermixing.

Card-Edge Lifting Structure (500)

One or more card-edge lifting structures (500) interleave the cards (600) of the first sub-stack (610) and the second sub-stack (620) by lifting an edge of the first sub-stack (610) and an edge of the second sub-stack (620) by vertical translation. For example, one or more card-edge lifting structures (500) interleave the cards (600) of the first sub-stack (610) and the second sub-stack (620) by lifting the second edge (614) of the first sub-stack (610) and the first edge (622) of the second sub-stack (620). Each card-edge lifting structure (500) comprises a shaft (520) and a means to linearly translate the card-edge lifting structure (910). Each card-edge lifting structure (500) may further comprise a card separator wall (510). Each card-edge lifting structure (500) may further comprise a pivot connection (540).

The card-edge lifting structure (500) may lift both edges at a time—the second edge (614) of the first sub-stack (610) and the first edge (622) of the second sub-stack (620) ("bi-edge lifting").

The card-edge lifting structure (500) may lift one edge at a time, either the second edge (614) of the first sub-stack (610) or the first edge (622) of the second sub-stack (620) ("mono-edge lifting").

Bi-Edge Lifting

The card-edge lifting structure (500) may lift both edges at a time, that is, the second edge (614) of the first sub-stack (610) and the first edge (622) of the second sub-stack (620) ("bi-edge lifting").

When the card intermixing device (90) comprises one card-edge lifting structure (500) performing bi-edge lifting, the card-edge lifting structure (500) is either positioned: a) at the third edge (116) the first card-receiving surface (110) and the third edge (216) of the second card-receiving surface (210), or b) at the fourth edge (118) of the first card-receiving surface (110) and the fourth edge (218) of the second card-receiving surface (210). FIG. 6 shows the card-edge lifting structure (500) positioned at the third edge (116) the first card-receiving surface (110) and the third edge (216) of the second card-receiving surface (210).

Figure 7:
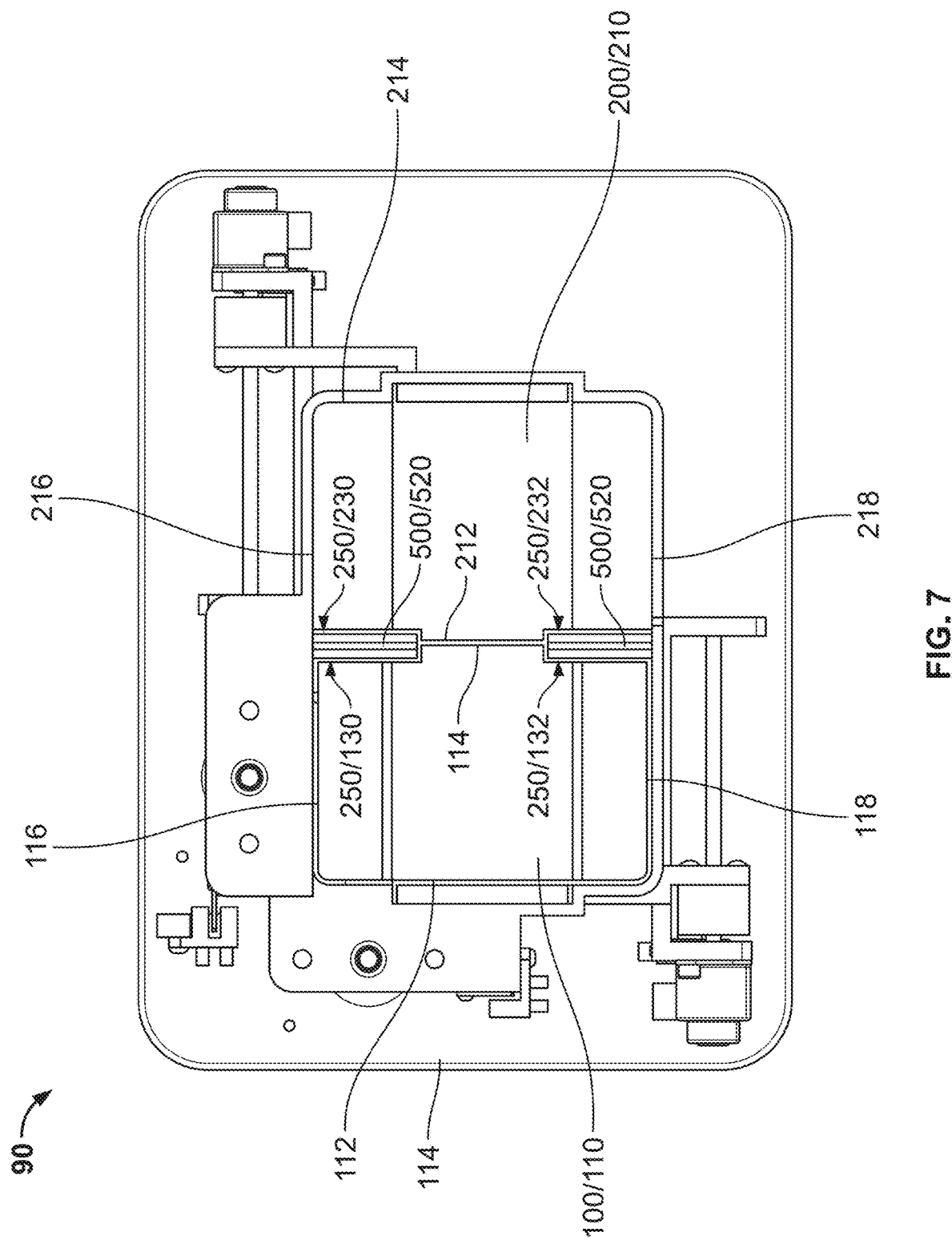
FIG. 7 shows a top sectional view of the housing (800), where the first card-receiving structure (100) is adjacent to the second card-receiving structure (200). The second-third edge notch (130) and the first-third edge notch (230) accommodate a card-edge lifting structure (500) along the third edge (116, 216) of the receiving surfaces. The second-fourth edge notch (132) and the first-fourth edge notch (232) accommodate a card-edge lifting structure (500) along the fourth edge (118, 218) of the receiving surfaces.

When the card intermixing device (90) comprises two card-edge lifting structures (500) performing bi-edge lifting, the card-edge lifting structures (500) are positioned: a) at the third edge (116) the first card-receiving surface (110) and the third edge (216) of the second card-receiving surface (210), and b) at the fourth edge (118) of the first card-receiving surface (110) and the fourth edge (218) of the second card-receiving surface (210). When two card-edge lifting structures (500) are present, the two card-edge lifting structures (500) may translate at the same velocity or they may translate at different velocities, creating variations in the card interleaving process. FIG. 7 shows a card-edge lifting structure (500) positioned at the third edge (116) the first card-receiving surface (110) and the third edge (216) of the second card-receiving surface (210), and a card-edge lifting structure (500) positioned at the fourth edge (118) of the first card-receiving surface (110) and the fourth edge (218) of the second card-receiving surface (210).

Mono-Edge Lifting

The card-edge lifting structure (500) may lift one edge at a time, either the second edge (614) of the first sub-stack (610) or the first edge (622) of the second sub-stack (620) ("mono-edge lifting").

In this mono-edge lifting configuration, a set of two card-edge lifting structures (500) are utilized: one card-edge lifting structure (500) lifts the second edge (614) of the first sub-stack (610) and another card-edge lifting structure (500) lifts the first edge (622) of the second sub-stack (620). The two card-edge lifting structures (500) may translate at the same velocity or they may translate at different velocities, creating variations in the card interleaving process.

When the card intermixing device (90) comprises one set of two card-edge lifting structures (500) performing mono-edge lifting, the set of two card-edge lifting structures (500) is positioned: a) at the third edge (116) the first card-receiving surface (110) and the third edge (216) of the second card-receiving surface (210), or b) at the fourth edge (118) of the first card-receiving surface (110) and the fourth edge (218) of the second card-receiving surface (210).

When the card intermixing device (90) comprises two sets of two card-edge lifting structures (500) performing mono-edge lifting, one set of two card-edge lifting structures (500) is positioned at the third edge (116) the first card-receiving surface (110) and the third edge (216) of the second card-receiving surface (210), and another set of two card-edge lifting structures (500) is positioned at the fourth edge (118) of the first card-receiving surface (110) and the fourth edge (218) of the second card-receiving surface (210). The card-edge lifting structures (500) may translate at the same velocity or they may translate at different velocities, creating variations in the card interleaving process.

Combination Mono and Bi-Edge Lifting

The card intermixing device (90) may comprise one card-edge lifting structure (500) performing bi-edge lifting and one set of two card-edge lifting structures (500) performing mono-edge lifting.

Gap (250)

For the one or more card-edge lifting structures (500) to lift the edges of the first sub-stack (610) and the second sub-stack (620), the shaft (520) of the card-edge lifting structure (500) needs to come into contact with the bottom (616) of the first sub-stack (610) and the bottom (626) of the second sub-stack (620). To accomplish this, one or more gaps (250) are located between the second edge (114) of the first card-receiving surface (110) and the first edge (212) of the second card-receiving surface (210).

The length and width of the gap (250) is sized to allow the shaft (520) of the card-edge lifting structure (500) to translate within the gap (250) upwards past the first card-receiving surface (110) and the second card-receiving surface (210) and come into contact with the bottom (616) of the first sub-stack (610) and bottom (626) of the second sub-stack (620).

Figure 16:
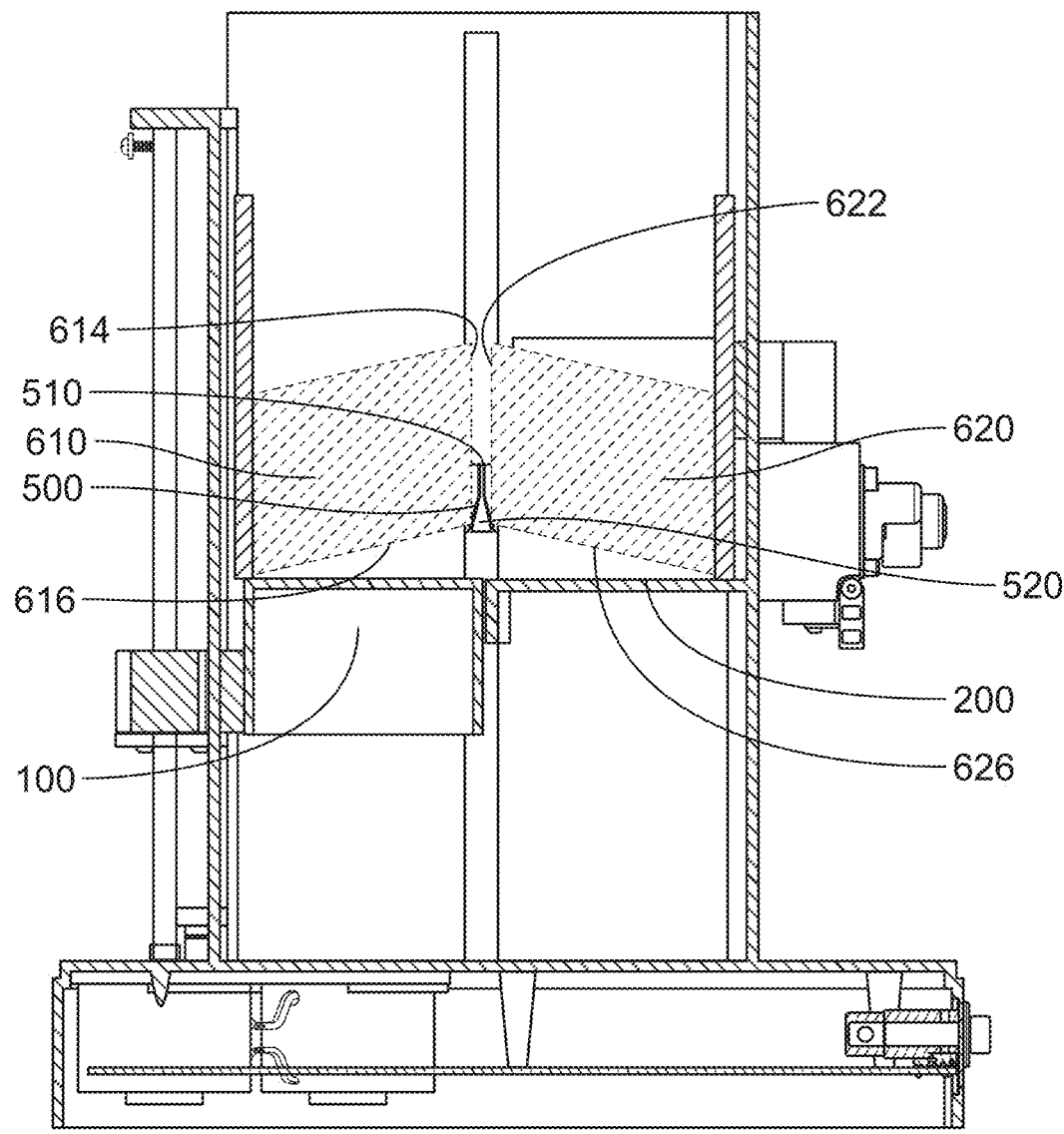
FIG. 16 shows a front sectional view of the housing (800), where the shaft (520) of the card-edge lifting structure (500) is being translated upwards, lifting the second edge (614) of the first sub-stack (610) and the first edge (622) of the second sub-stack (620).
Figure 17:
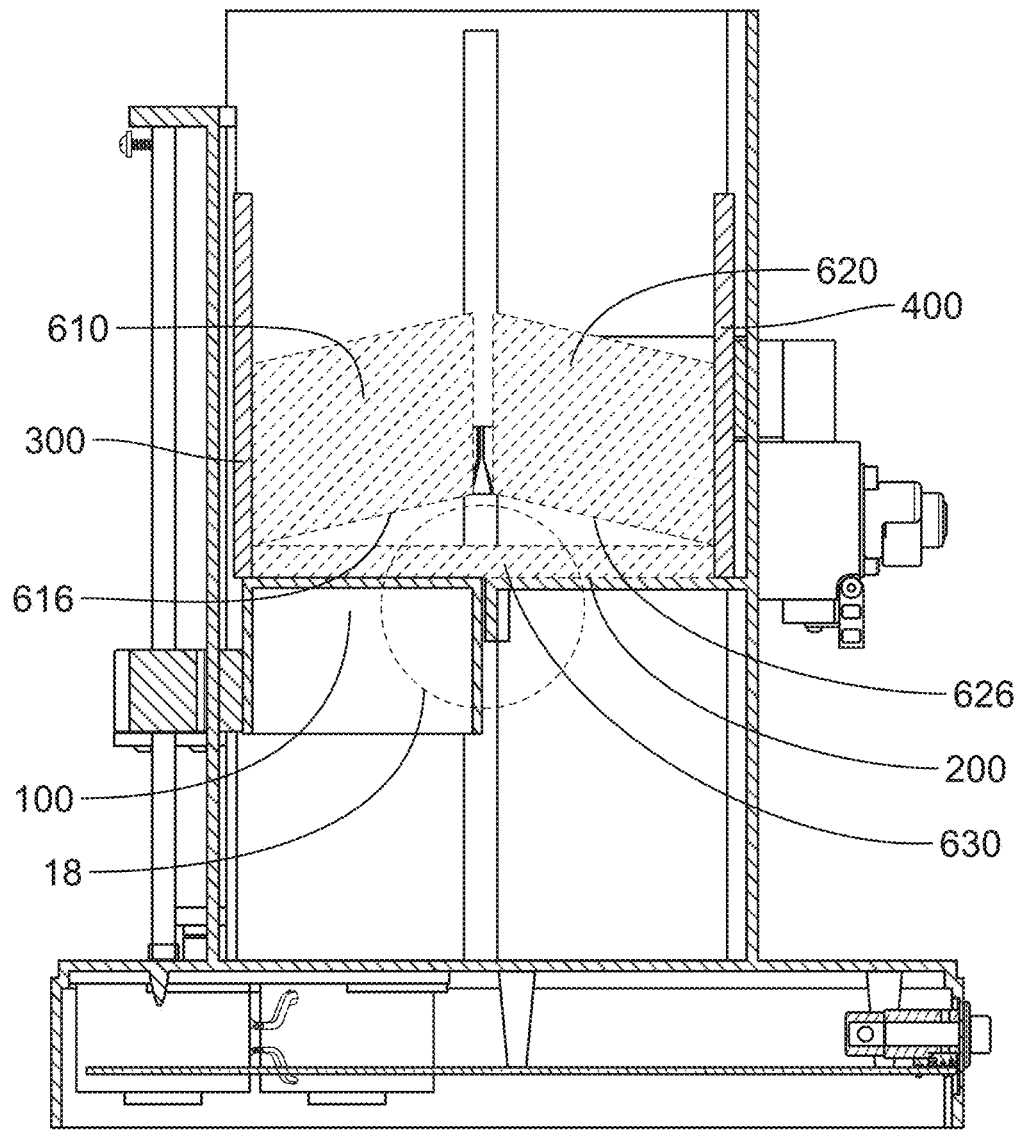
FIG. 17 shows a front sectional view of the housing (800), where the cards (600) from the bottom (616) of the first sub-stack (610) and cards (600) from the bottom (626) of the second sub-stack (620) have fallen past the shaft (520) and interleaved into an interleaved card stack (630).

The shaft (520) may be positioned so that the shaft (520) to comes into contact symmetrically with the bottom (616) of the first sub-stack (610) and the bottom (626) of the second sub-stack (620). FIG. 16 shows the shaft (520) translating through the gap (250), allowing the shaft (520) to come into contact symmetrically with the bottom (616) of the first sub-stack (610) and bottom (626) of the second sub-stack (620). Alternatively, the shaft (520) may be positioned so that the shaft (520) comes into contact asymmetrically with the bottom (616) of the first sub-stack (610) and bottom (626) of the second sub-stack (620). This creates an amount of asymmetry in the card falling and interleaving for the first sub-stack (610) relative to the second sub-stack (620). FIG. 17 shows the shaft (520) translating through the gap (250), allowing the shaft (520) to come into contact asymmetrically with the bottom (616) of the first sub-stack (610) and bottom (626) of the second sub-stack (620).

The gap (250) may span the entirety of the second edge (114) of the first card-receiving surface (110) and the first edge (212) of the second card-receiving surface (210).

Alternatively, the gap (250) may span a portion of the second edge (114) of the first card-receiving surface (110) and the first edge (212) of the second card-receiving surface (210). For instance, corner notches may be added to the first card-receiving surface (110) and the second card-receiving surface (210). The first card-receiving surface (110) may further comprise a second-third edge notch (130) located at the corner of the second edge (114) and the third edge (116), and/or a second-fourth edge notch (132) located at the corner of the second edge (114) and the fourth edge (118). The second card-receiving surface (210) may further comprise a first-third edge notch (230) located at the corner of the first edge (212) and the third edge (216) and/or a first-fourth edge notch (232) located at the corner of the first edge (212) and the fourth edge (218). The corner notches of first card-receiving surface (110) relative to the corner notches of the second card-receiving surface (210) may be symmetrical or may be asymmetrical.

As a first example, the first card-receiving surface (110) has a second-third edge notch (130) and the second card-receiving surface (210) has a first-third edge notch (230). The second-third edge notch (130) and the first-third edge notch (230) accommodate a card-edge lifting structure (500) along the third edge (116, 216) of the receiving surfaces. FIG. 6 shows a top sectional view of the housing (800), where the second-third edge notch (130) and the first-third edge notch (230) accommodate a card-edge lifting structure (500).

As a second example, the first card-receiving surface (110) has a second-fourth edge notch (132) and the second card-receiving surface (210) has a first-fourth edge notch (232). The second-fourth edge notch (132) and the first-fourth edge notch (232) accommodate a card-edge lifting structure (500) along the fourth edge (118, 218) of the receiving surfaces.

As a third example, a combination of the first example and the second example accommodates a card-edge lifting structure (500) along the third edge of the receiving surfaces (116, 21) and a card-edge lifting structure (500) along the fourth edge (118, 218) of the receiving surfaces. FIG. 7 shows a top sectional view of the housing (800), where the first card-receiving structure (100) is adjacent to the second card-receiving structure (200). The second-third edge notch (130) and the first-third edge notch (230) accommodate a card-edge lifting structure (500) along the third edge (116, 216) of the receiving surfaces. The second-fourth edge notch (132) and the first-fourth edge notch (232) accommodate a card-edge lifting structure (500) along the fourth edge (118, 218) of the receiving surfaces.

Shaft (520)

Figure 12A:
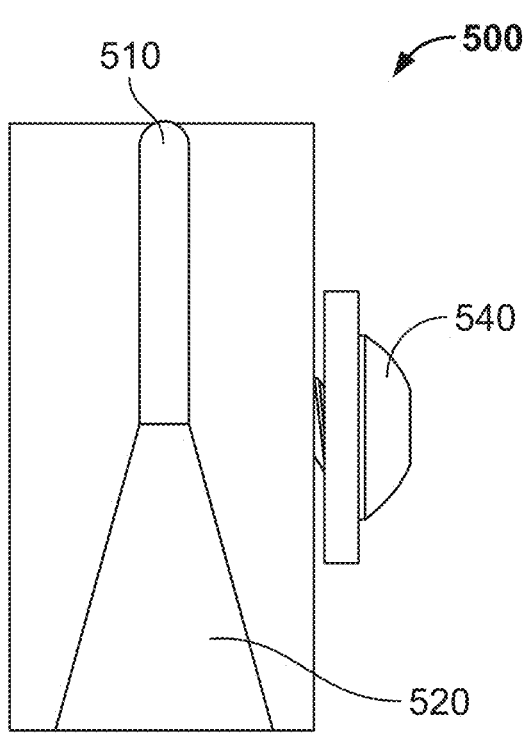
FIG. 12(A) shows a card edge lifting structure (500) with a triangular cross section shaft (520)
Figure 12B:
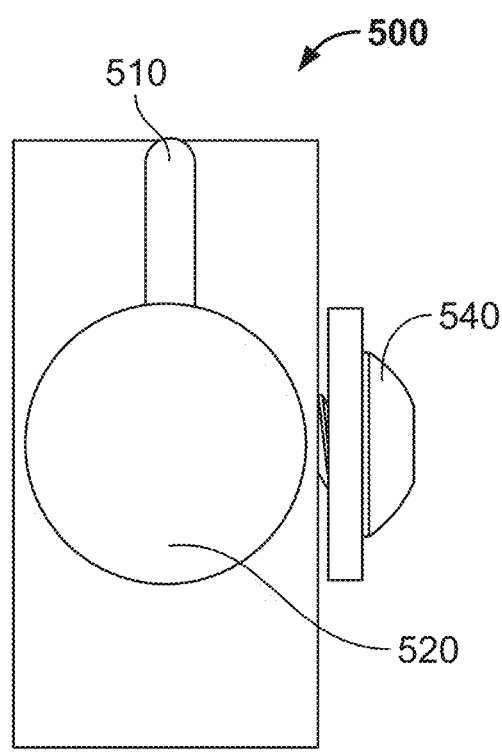
FIG. 12(B) shows a card edge lifting structure (500) with a circular cross section shaft (520)
Figure 12C:
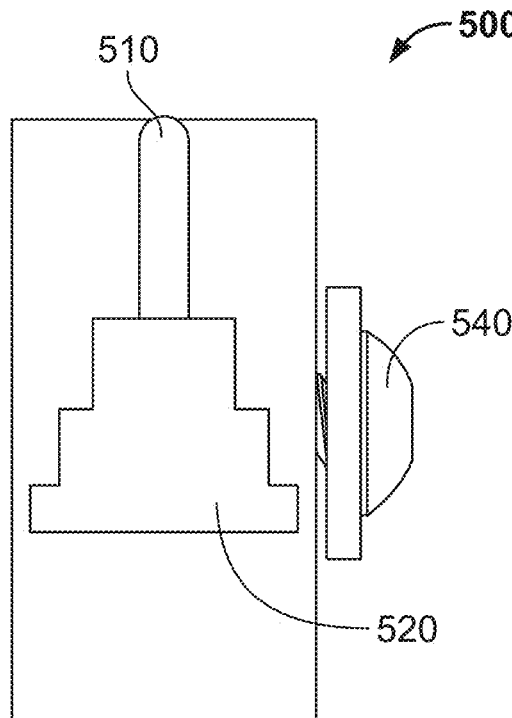
FIG. 12(C) shows a card edge lifting structure (500) with a step cross section shaft (520)
Figure 12D:
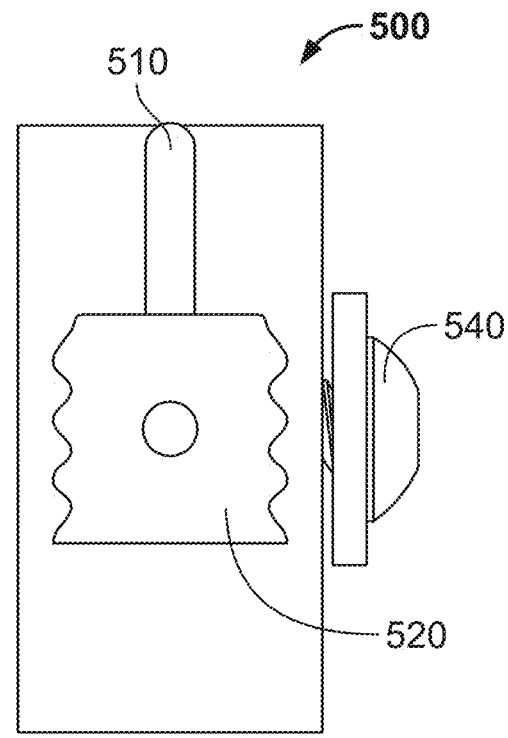
FIG. 12(D) shows a card edge lifting structure (500) with a knob cross section shaft (520).

The shaft (520) lifts the second edge (614) of the first sub-stack (610) and the first edge (622) of the second sub-stack (620). Because the manner of the card (600) falling and interleaving is dependent on the shape of card-edge lifting structure (500), care is needed to select the most appropriate shaft (520) shape. Polyhedron (e.g. rectangular prisms) and non-polyhedron (e.g. cylinders, cones, spheres) shapes may be utilized. Regular (e.g. cubes) and irregular polyhedron (e.g. prisms) shapes may be utilized. The card falling and interleaving is better controlled when the cross section of the shaft (520) is congruent along its central axis. FIGS. 12 (A)-(D) show a front view of the card-edge lifting structure (500) comprising a shaft (520), a card separator wall (510), and a pivot connection (540). FIG. 12(A) shows a card edge lifting structure (500) with a triangular cross section shaft (520), FIG. 12(B) shows a card edge lifting structure (500) with a circular cross section shaft (520), FIG. 12(C) shows a card edge lifting structure (500) with a step cross section shaft (520), FIG. 12(D) shows a card edge lifting structure (500) with a knob cross section shaft (520).

Figure 11:
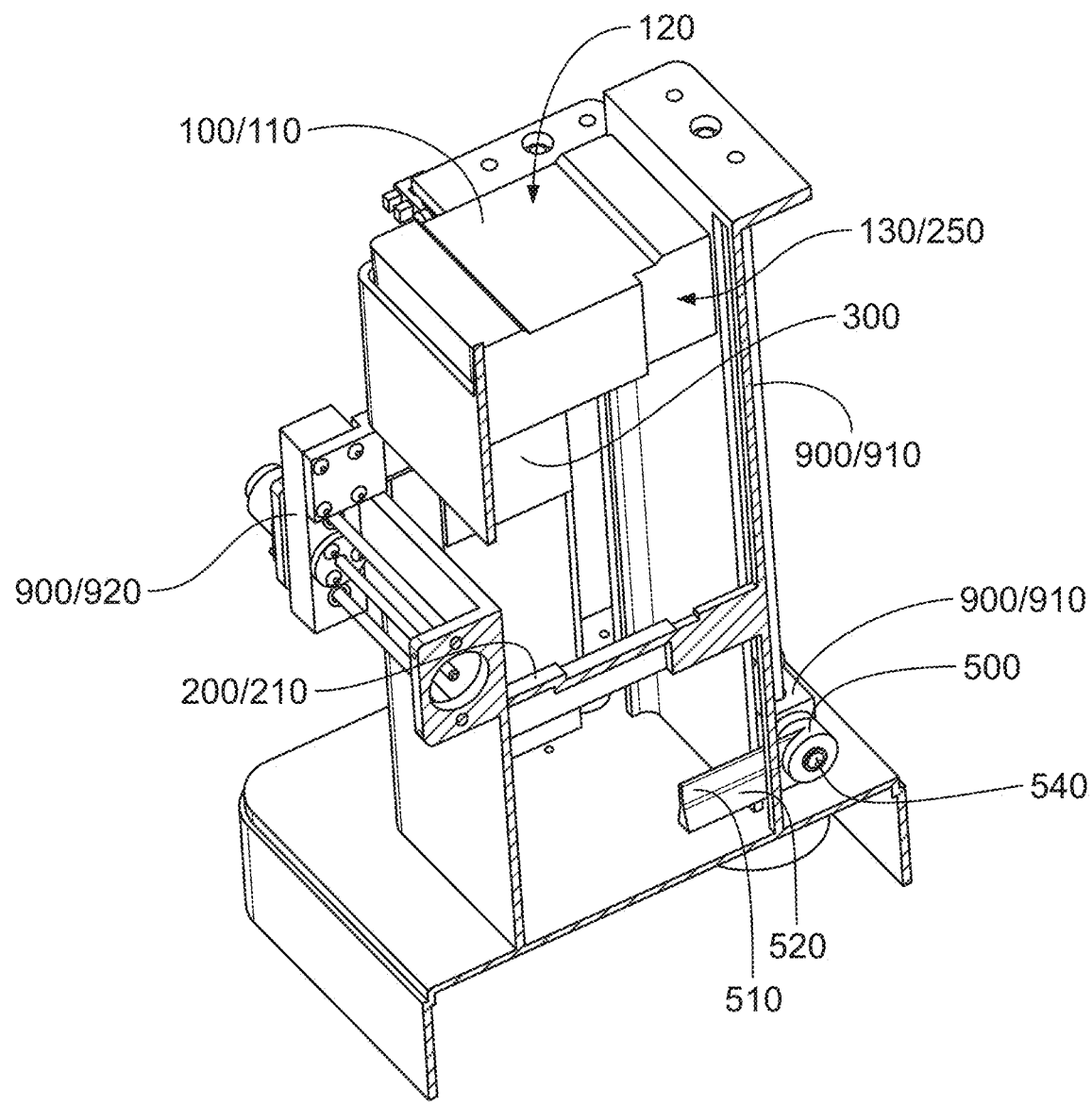
FIG. 11 shows a perspective view of the card intermixing device (90) of the elements within the housing (800) (not shown). The card-edge lifting structure (500) is positioned within the gap (250) located between the first card-receiving surface (110) and the second card-receiving surface (210). The means to linearly translate the card-edge lifting structure (910) is connected to the card-edge lifting structure (500).

Given their regularity and symmetry, prisms and cylinders are preferred shapes for the shaft (520). A prism is defined as a polyhedron with a first n-sided polygonal base, a second base which is a translated copy of the first base, and n other faces (necessarily all parallelograms) joining corresponding sides of the two bases. Prism structures include triangular prisms and hexagonal prisms. FIG. 11 shows a perspective view of the card intermixing device (90), where the shaft (520) is in the shape of a triangular prism.

The shaft (520) may have a symmetrical cross section or it may have an asymmetrical cross section with reference to the card separator wall (510). A symmetrical cross section allows for a more controlled interleaving of the cards (600) of the first sub-stack (610) and the second sub-stack (620). An asymmetrical cross section with reference to the card separator wall (510) allows the cards (600) from both sides to fall differently, increasing card falling randomness, as described below.

The shaft (520) is oriented so that the shaft (520) can vertically translate within the one or more gaps (250) located between the first card-receiving surface (110) and the second card-receiving surface (210) ("lifting orientation"). FIG. 11 shows a perspective view of the card intermixing device (90) and the elements within the housing (800) (not shown). The card-edge lifting structure (500) is positioned within the gap (250) located between the first card-receiving surface (110) and the second card-receiving surface (210). The means to linearly translate the card-edge lifting structure (910) is connected to the card-edge lifting structure (500).

The shaft (520) is sized to fit within the gap (250) located between the second edge (114) of the first card-receiving surface (110) and the first edge (212) of the second card-receiving surface (210). The width of the shaft (520) is sized so that the shaft (520) comes into contact with some portion of the edges of the first sub-stack (610), the edges of the second sub-stack (620), or both. The length of the shaft (520) may span the entirety of the second edge (114) of the first card-receiving surface (110) and the first edge (212) of the second card-receiving surface (210). Alternatively, the length of the shaft (520) may span a portion of the second edge (114) of the first card-receiving surface (110) and the first edge (212) of the second card-receiving surface (210).

If the card-edge lifting structure (500) comprises a pivot connection (540), the shaft (520) is pivotally connected to the means to linearly translate the card-edge lifting structure (910). Once all the cards (600) from the first sub-stack (610) and the second sub-stack (620) have fallen, the shaft (520) stops translating upward. The shaft (520) pivots upwards, downwards, or sideways, to move out of the way so that the card-edge lifting structure (500) can translate downwards without hitting the interleaved card-stack (630). Once the card-edge lifting structure (500) has been lowered past the interleaved card-stack (630), the first card-receiving surface (110), and the second card-receiving surface (210), the card-edge lifting structure (500) stops translating downward, and the shaft (520) pivots back to the lifting orientation. This allows the card-edge lifting structure (500) to perform the card intermixing process repeatedly and automatically.

Alternatively, the card-edge lifting structure (500) may remain positioned above the interleaved card-stack (630) until the interleaved card-stack (630) is being "squared up." At that point, the card-edge lifting structure (500) is lowered until the shaft (520) is positioned above the top (632) of the interleaved card-stack (630) to constrain the upward movement of cards (600) from the interleaved card-stack (630) should these cards (600) try to "rise" as the interleaved card-stack (630) is being "squared up." The shaft (520) is a physical constraint to the upward movement of cards (600) located on the top (632) of the interleaved card-stack (630). Once the interleaved card-stack (630) is "squared up," the card-edge lifting structure (500) proceeds as described in the previous paragraph.

If the card-edge lifting structure (500) does not comprise a pivot connection (540), the downward translation of the card-edge lifting structure (500) is accomplished differently. Once all the cards (600) from the first sub-stack (610) and the second sub-stack (620) have fallen, the shaft (520) stops translating upward. The card-edge lifting structure (500) remains in this position until the card stack (605) has been "squared up" and repositioned onto the first card-receiving surface (110). At this point, the card-edge lifting structure (500) translates downward past the card stack (605) through the one or more gaps (250).

Card Separator Wall (510)

The card separator wall (510) has three functions: a) separates the first sub-stack (610) from the second sub-stack (620) as the shaft (520) vertically translates upwards, b) maintains the second edge (614) of the first sub-stack (610) substantially flush against the card separator wall (510) when the first push surface (300) translates towards the second edge (114) of the first card-receiving surface (110), and c) maintains the first edge (622) of the second sub-stack (620) substantially flush against the card separator wall (510) when the second push surface (400) translates towards the first edge (212) of the second card receiving surface (210), allowing for a more controlled card falling process.

The card separator wall (510) is oriented vertically along the axis of motion of the shaft (520). The card separator wall (510) is connected to the shaft (520) on a surface of the shaft (520) that faces upwards.

Interleaving

The interleaving of the cards (600) of the first sub-stack (610) and the second sub-stack (620) begins by having the shaft (520) positioned below the first card-receiving surface (110) and the second card-receiving surface (210). The shaft (520) is translated upwards by the means to linearly translate the card-edge lifting structure (910). Once the shaft (520) comes into contact with the bottom (616) of the first sub-stack (610) or bottom (626) of the second sub-stack (620) or both, the shaft (520) continues to translate upward, lifting the second edge (614) of the first sub-stack (610) and the first edge (622) of the second sub-stack (620). FIG. 16 shows a front sectional view of the housing (800), where the shaft (520) of the card-edge lifting structure (500) is being translated upwards, lifting the second edge (614) of the first sub-stack (610) and the first edge (622) of the second sub-stack (620).

As the shaft (520) translates upward, the first push surface (300) translates towards the second edge (114) of the first card-receiving surface (110) so that the first sub-stack (610) is pushed, and the second push surface (400) translates towards the first edge (212) of the second card-receiving surface (210) so that the second sub-stack (620) is pushed. These movements push the first sub-stack (610) and the second sub-stack (620) towards each other. These movements force the second edge (614) of the first sub-stack (610) and the first edge (622) of the second sub-stack (620) to interleave when the cards (600) from the first sub-stack (610) and the second sub-stack (620) fall. FIG. 16 shows the first push surface (300) translating towards the second edge (114) of the first card-receiving surface (110) so that the first sub-stack (610) is pushed, and the second push surface (400) translating towards the first edge (212) of the second card-receiving surface (210) so that the second sub-stack (620) is pushed.

When the shaft (520) reaches a certain height relative to the first card-receiving surface (110) and the second card-receiving surface (210), the edges of the cards (600) at the bottom (616) of the first sub-stack (610) and the bottom (626) of the second sub-stack (620) fall past the shaft (520).

Figure 18:
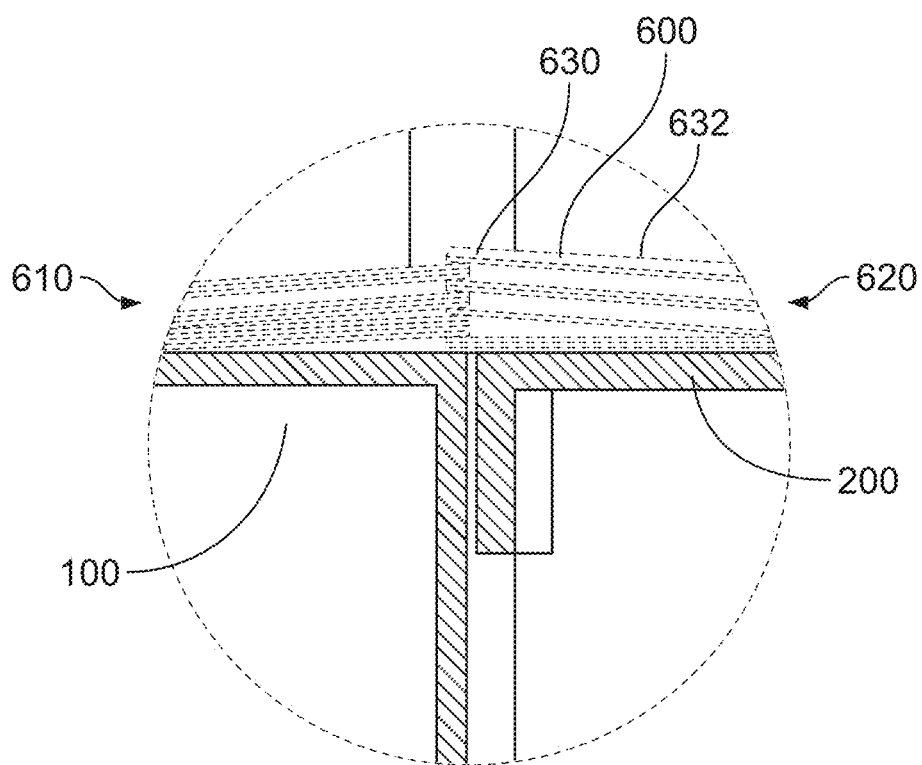
FIG. 18 shows an enlarged view of the interleaved card stack (630), where cards (600) from the first sub-stack (610) and cards (600) from the second sub-stack (620) have been interleaved into an interleaved card stack (630).
Figure 19:
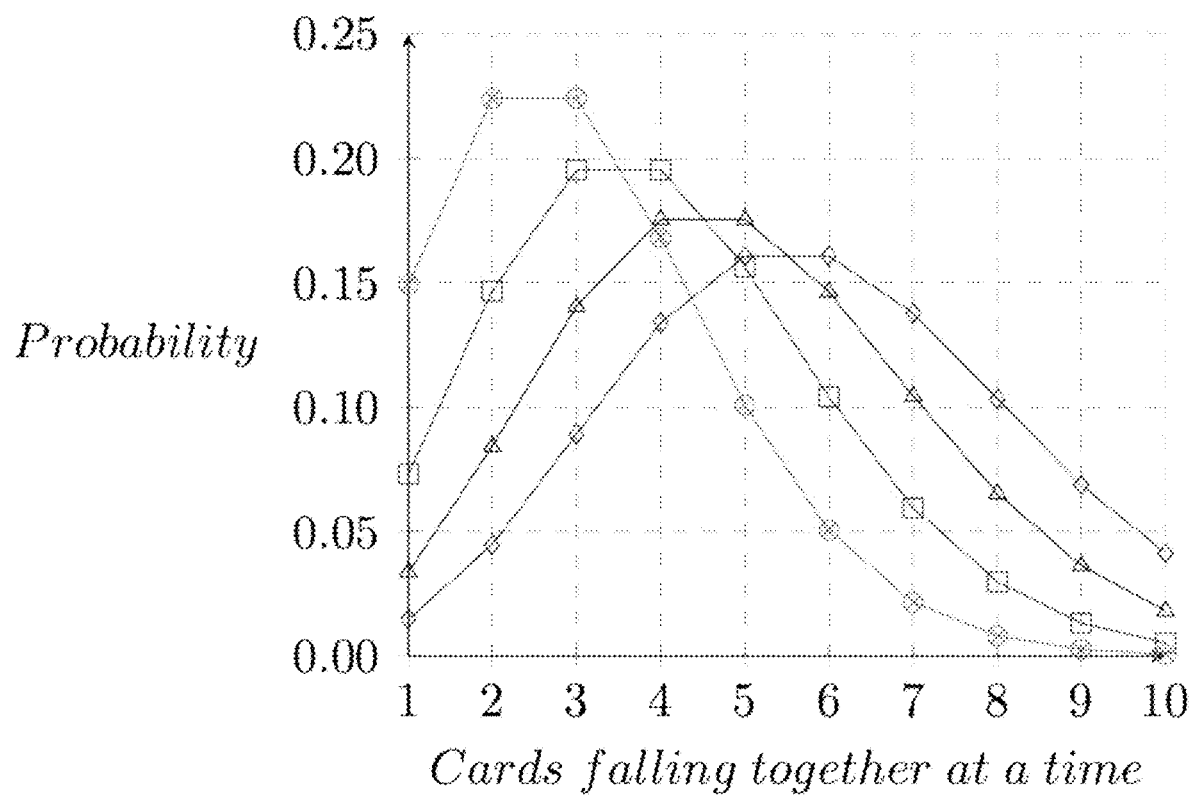
FIG. 19 illustrates various example probability distributions for the number of cards (600) that fall together at a time.

As the cards (600) fall, the cards (600) from the first sub-stack (610) and the second sub-stack (620) interleave, creating an interleaved card stack (630). The shaft (520) continues to lift until all the cards (600) from the first sub-stack (610) and the second sub-stack (620) fall past the shaft (520). This interleaving process positions the cards (600) partly onto each other. It is necessary to "square up" the cards (600) to position the cards (600) fully onto each other. FIG. 17 shows a front sectional view of the housing (800), where cards (600) from the bottom (616) of the first sub-stack (616) and cards (600) from the bottom (626) of the second sub-stack (620) have fallen past the shaft (520) and interleaved into an interleaved card stack (630). FIG. 18 shows an enlarged view of the interleaved card stack (630), where cards (600) from the first sub-stack (610) and cards (600) from the second sub-stack (620) have been interleaved into an interleaved card stack (630).

As the cards (600) fall and the shaft (520) translates upward, the first push surface (300) may continue to translate towards the second edge (114) of the first card-receiving surface (110) and the second push surface (400) may continue to translate towards the first edge (212) of the second card-receiving surface (210). This translation maintains the second edge (614) of the first sub-stack (610) substantially flush against the card separator wall (510) and the first edge (622) of the second sub-stack (620) substantially flush against the card separator wall (510). This allows for a more controlled card falling process.

Card Falling Randomness

The cards (600) do not necessarily fall past the shaft (520) one at a time. It has been observed through extensive testing that the number of cards (600) falling at one time from the bottom (616) of the first sub-stack (610) and the bottom (626) of the second sub-stack (620) follows a random distribution from one to five or more cards. This card falling randomness allows the interleaving to be random, similar to a manual riffle shuffle. This card falling randomness eliminates faro shuffle concerns. This card falling randomness is caused by various effects including surface tension, micro-stacking friction, and surface humidity differentials.

This card falling randomness can be augmented in a number of ways. The vertical translating speed of the card-edge lifting structure (500) can be constant or be changed as the card-edge lifting structure (500) translates upward; this speed change can be constant or variable. The speed changes can be pre-determined or random.

Card vibration can be introduced by the various elements involved in the interleaving such as the card-edge lifting structure (500), the first push surface (300), and the second push surface (400). For example, the card-edge lifting structure (500) may further comprise a card-edge vibration actuator (550), where the card-edge vibration actuator (550) is connected to the shaft (520). When the card-edge vibration actuator (550) causes the shaft (520) to vibrate as it lifts, the vibration imparts additional forces upon the sub-stacks that modify the card falling randomness.

As another example, the first push surface (300) may further comprise a first push surface vibration actuator (320) and the second push surface (400) may further comprise a second push surface vibration actuator (420). The first push surface vibration actuator (320) is connected to the first push surface (300). The second push surface vibration actuator (420) is connected to the second push surface (400). When the first push surface vibration actuator (320) causes the first push surface (300) to vibrate, the vibration imparts additional forces upon the first sub-stack (610) as the first push surface (300) translates the first sub-stack (610). When the second push surface vibration actuator (420) causes the second push surface (400) to vibrate, the vibration imparts additional forces upon the second sub-stack (620) as the second push surface (400) translates the second sub-stack (620).

As another example, the means to linearly translate an object (900) may impart vibration. The means to linearly translate the card-edge lifting structure (910) may impart vibration upon the shaft (520). The means to linearly translate the first push surface (920) may impart vibration upon the first push surface (300). The means to linearly translate the second push surface (930) may impart vibration upon the second push surface (400).

The vibration actuators are operatively connected to the computer controller (1000). The computer controller (1000) determines the vibration presence, amount, and duration.

Free-Falling Vs. Added-Force-Falling

The basic upward translation by the card-edge lifting structure (500) causes the cards (600) to free-fall when the edges of the cards (600) at the bottom (616) of the first sub-stack (610) and the bottom (626) of the second sub-stack (620) fall past the shaft (520). Free-falling is defined as the motion of an object where the only force acting upon an object is gravity.

Additional forces may be added to gravity to alter the falling of the cards (600) from the first sub-stack (610) and the second sub-stack (620). Added-force-falling is defined as the motion of an object where there are one or more additional forces added to gravity to act upon an object.

Added-force-falling may be added with force generating systems such as pneumatics and elastics.

Added-force-falling can also be introduced to the cards (600) by altering the motion of the first push surface (300) and the second push surface (400). The first push surface (300) and the second push surface (400) can translate the first sub-stack (610) and the second sub-stack (620) so that the cards (600) push against the card separator wall (510) introducing compression, torsion, tension, shear, and bending forces. These forces impart upon the cards (600) energy that is released as the card falls from the shaft (520). This released energy alters the card interleaving.

Squaring Up and Repositioning

Once all the cards (600) from the first sub-stack (610) and the second sub-stack (620) have fallen, interleaving into an interleaved card stack (630), the interleaved card stack (630) is "squared up" into the card stack (605) and the card stack (605) repositioned to continue the card intermixing process or to finish the card intermixing process. There are at least two methods to "square up" the interleaved card stack (630) into the card stack (605) and to reposition the card stack (605) to continue or end the card intermixing process.

The first method involves separate squaring up and repositioning steps. To "square up" the interleaved card stack (630) from the first sub-stack (610) and the second sub-stack (620) into the card stack (605), the first push surface (300) translates towards the second edge (114) of the first card-receiving surface (110) so that cards (600) from the first sub-stack (610) are pushed. The second push surface (400) translates towards the first edge (212) of the second card-receiving surface (210) so that cards (600) from the second sub-stack (620) are pushed. These movements force the interleaved card stack (630) from the first sub-stack (610) and the second sub-stack (620) to be fully positioned onto each other, "squaring up" the interleaved card stack (630) into the card stack (605). Once the interleaved card stack (630) has been "squared up" into the card stack (605), the card stack (605) is repositioned onto the first card-receiving surface (110). The first push surface (300) returns to its initial first push surface position, that is, the first push surface (300) translates towards the first edge (112) of the first card-receiving surface (110) until the first push surface (300) is adjacent to the first card-receiving surface (110). The second push surface (400) translates towards the first push surface (300), moving the card stack (605) until the interleaved card stack (630) is repositioned onto the first card-receiving surface (110) and the interleaved card stack (630) is "squared up" into the card stack (605). The second push surface (400) then translates back to its initial second push surface position.

The second method allows for the "squaring up" and the repositioning to occur at the same time. To "square up" the interleaved card stack (630) from the first sub-stack (610) and the second sub-stack (620) into the card stack (605) and to reposition the card stack (605), the first push surface (300) returns to its initial first push surface position; the first push surface (300) translates towards the first edge (112) of the first card-receiving surface (110) until the first push surface (300) is adjacent to the first card-receiving surface (110). The second push surface (400) translates towards the first push surface (300), moving the card stack (605) until the interleaved card stack (630) is repositioned onto the first card-receiving surface (110) and the interleaved card stack (630) is "squared up" into the card stack (605). The second push surface (400) then translates back to its initial second push surface position.

When the card stack (605) is repositioned onto the first card-receiving surface (110), the intermixing process is completed and counted as one (1) intermixing cycle.

Cycling Through

Once the card stack (605) has been repositioned onto the first card-receiving surface (110), either a) the intermixing of the cards (600) is completed or b) the intermixing of the cards (600) continues and the card stack (605) goes through another intermixing cycle of the intermixing process.

When the intermixing of the cards (600) is completed, the card stack (605) is translated for removal from the housing (800). This translation may be automatic or on-demand. An on-demand option allows the card stack (605) to remain within the housing (800) after intermixing to eliminate the potential of the card stack (605) being hit and knocked over or being tampered. This on-demand option may be activated through the interface operatively connected to the computer controller (1000).

When the housing (800) comprises a top surface (820) and a top aperture (810), the first card-receiving surface (110) is translated vertically so that the card stack (605) can be accessed through the top aperture (810) of the top surface (820) of the housing (800). The card stack (605) emerges from the housing (800) and the dealer can remove the card stack (605) from the first card-receiving surface (110). If the second shape (814) of the top aperture (810) is present, the second shape (814) of the top aperture (810) and the finger notch (122) of the first card-receiving surface (110) allow the dealer to place a finger or a thumb under the card stack (605) for easier removal. If the card funnel (830) is present, the card stack (605) emerges through the top aperture (810) and the bottom opening (834) of the card funnel (830).

When the housing (800) comprises a side surface (860) and a side aperture (870), the first card-receiving surface (110) is translated vertically so that the card stack (605) can be accessed through the side aperture (870) of the side surface (860) of the housing (800).

If the intermixing of the cards (600) continues, the first card-receiving surface (110) is translated vertically by the means to linearly translate the first card-receiving surface (940) so that a portion of the card stack (605) is aligned below the bottom edge (310) of the first push surface (300) (the first sub-stack (610)) and a portion of the card stack (605) is aligned above the bottom edge (310) of the first push surface (300) (the second sub-stack (620)). The intermixing process continues as described previously in the 13th Paragraph of SubSection Inside the Housing (800).

The card intermixing device (90) may be programmed to intermix the cards (600) of the card stack (605) repeatedly and automatically. The number of intermixing cycles that the card stack (605) goes through is pre-determined to ensure an adequately randomized card stack (605).

The randomness of the intermixing of the cards (600) can be adjusted in a number of ways. First, the number of intermixing cycles can be changed, typically ranging from three to nine intermixing cycles. Second, the speed of the vertical translation of the shaft (520) might change depending on the number of cards (600) in the card stack (605)— e.g. it might take a second or two to go through an intermixing cycle with a single deck or up to twenty seconds or more with six to ten decks. Third, the speed of the vertical translation of the shaft (520) might differ—up to twenty seconds or more—in any given intermixing cycle, with the speed changes being predetermined or randomly determined. These features may be set by house management through an interface.

Means to Sanitize Cards (700)

The Pandemic of 2019 has demonstrated that the COVID virus is highly infectious with high morbidity outcomes. To handle these characteristics, the entire fabric of society has been unwound and rewoven to ensure its survival. In other words, this Pandemic resulted in a "new normal" being established. Sanitation practices for people and objects alike have been rethought, becoming more rigorous and thorough, as any high traffic, visible surface is a potential source of exposure and potential infection.

In this context, the handling of playing cards in casinos should be considered a serious source for exposure, as any given card in casino games such as poker and blackjack can be handled upwards of several hundred times in a 24-hour time period. Playing cards are potentially contaminated during each and every hand being played. For example, at poker or blackjack, when a player sits for hours (as often the norm), literally "hundreds" of people will be touching the playing cards at just one session of playing.

Furthermore, the design of current card shuffling machines actually ensures that "exposed" cards are intermixed with other cards, creating an extreme threat of virus and bacteria transmission. Current card shuffling machines are complex with multiple pathways, gears, pulleys, and slots, making them hard, expensive, and time consuming to clean to prescribed sanitary levels.

The card interleaving allowed by the card intermixing device (90) does away with the sanitary limitations of current card shuffling machines. There is a minimum of complex, moving parts, but more importantly, the card interleaving creates opportunities for cards (600) to be sanitized while the card stack (605) is being intermixed.

A means to sanitize cards (700) can include a variety of physical mechanisms, individually or in combination. For instance, cards can be subject to electromagnetic radiation generated for example by an infrared or ultraviolet ray generator. Current research suggests that a sustained exposure of electromagnetic radiation can decrease activity by upwards of 80%.

Another approach to a means to sanitize cards (700) is to immerse the cards through a gas bath created by a gas generator. A suitable sanitizing gas, for example, can include a concentration of ozone, generated by an ozone generator. Ozone sterilization is commonly used in hospitals to sanitize equipment and significantly reduce or eliminate the spread of bacteria. Coronaviruses are classified as "enveloped viruses", which are typically more susceptible to "physicochemical challenges" such as ozone. Ozone kills this virus type by breaking through the outer shell into the core, resulting in damage to the viral RNA. Ozone can also damage the outer shell of the virus in a process called oxidation. Put simply, exposing Coronaviruses to sufficient ozone doses can result in them being 99% damaged or destroyed. CPAP ozone sterilizers claim in excess of 99.9% sterilization.

As the cards (600) of the card stack (605) fall from the shaft (520), the front and back sides of the cards are exposed to the atmosphere within the housing (800). Having the means to sanitize cards (700) within the housing (800) allows for the buildup of an effective concentration of gases or the emission of an effective amount of electromagnetic radiation to sanitize the cards (600). This means to sanitize cards (700) can range from a few second exposure to a continuous exposure while the card stack (605) is being intermixed. FIG. 9 shows a front sectional view of the housing (800), where the means to sanitize cards (700) is located at the bottom of the housing (800).

Means to Linearly Translate an Object (900)

The means to linearly translate an object (900) is a device that uses a prime mover (970), such as electro-mechanics, pneumatics, hydraulics, to provide linear motion, allowing the object to linearly translate.

An example of such a device is a linear actuator (960). A linear actuator (960) includes mechanical actuators, hydraulic actuators, pneumatic actuators, piezoelectric actuators, twisted and coiled polymer (TCP) actuators, electro-mechanical actuators, linear motors, and telescoping linear actuators. https:en.wikipedia.orgwikiLinear_actuator The linear actuator (960) may also comprise guideways (980). The linear actuator (960) may be closed looped or open looped. The linear actuator (960) may also comprise optical sensors (990) that track the location of the means to linearly translate an object (900).

When an electro-mechanical actuator is used, a variety of rotary motor (972) prime movers (970) may be used, including stepper motors. Stepper motors allow for small, finite, precise movements. In combination with the computer controller (1000), a stepper motor can achieve very precise positioning and/or speed control. Stepper motors have the ability to move forward and reverse in tiny increments to impart vibration.

The card intermixing device (90) comprises four separate means to linearly translate an object (900): a means to linearly translate the first card-receiving structure (940), a means to linearly translate the card-edge lifting structure (910), a means to linearly translate the first push surface (920), and a means to linearly translate the second push surface (930). The card intermixing device (90) may further comprise a means to linearly translate the second receiving surface.

The means to linearly translate the first card-receiving structure (940) is connected to the first card-receiving structure (100). The means to linearly translate the card-edge lifting structure (910) is connected to the card-edge lifting structure (500). The means to linearly translate the first push surface (920) is connected to the first push surface (300). The means to linearly translate the second push surface (930) is connected to the second push surface (400). The means to linearly translate the second receiving surface is connected to the second card-receiving structure (200).

Figure 10:
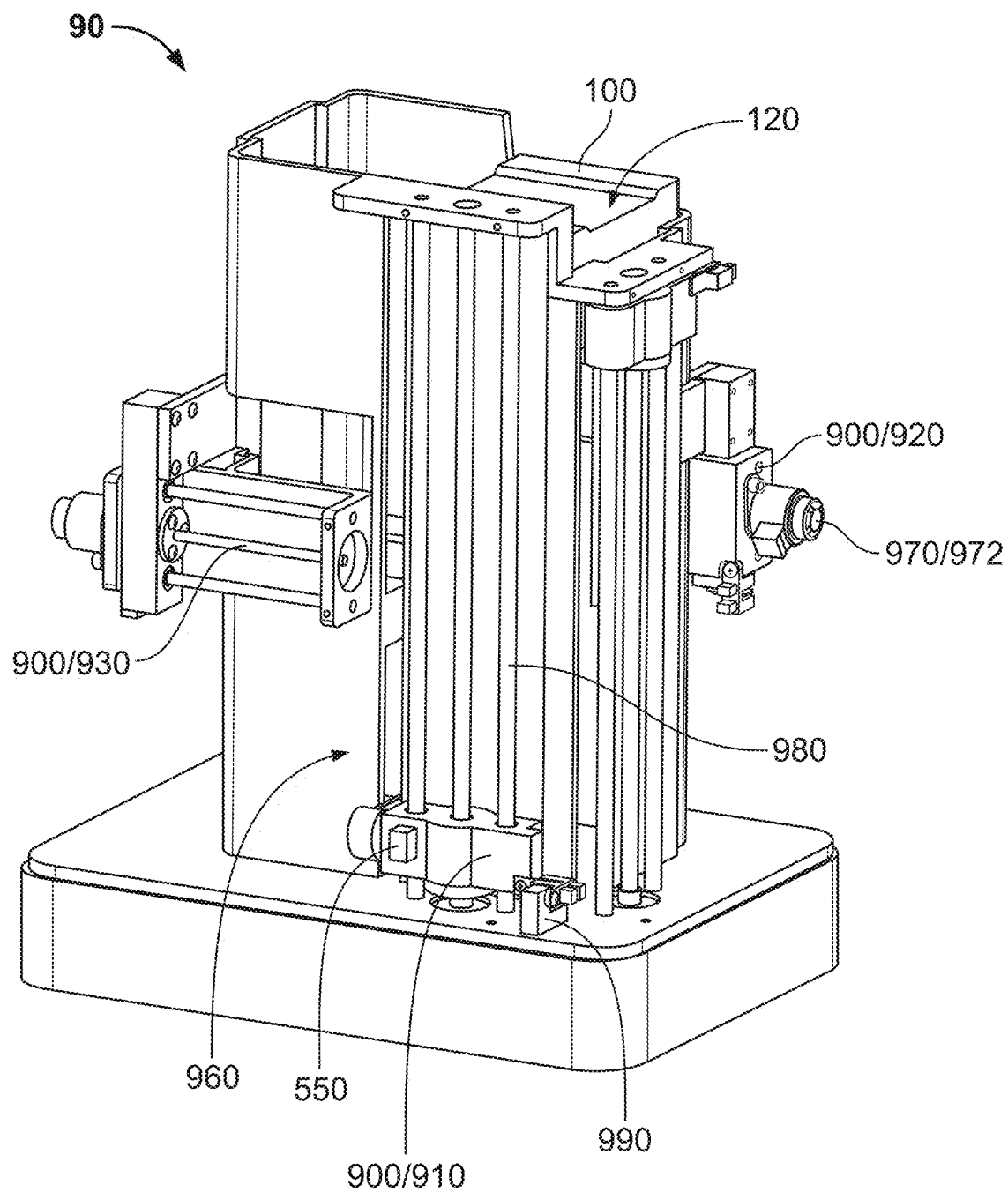
FIG. 10 shows a perspective view of the card intermixing device (90) and the elements within the housing (800) (not shown). Four separate means to linearly translate an object (900) are shown: a means to linearly translate the first card-receiving structure (940), a means to linearly translate the card-edge lifting structure (910), a means to linearly translate the first push surface (920), and a means to linearly translate the second push surface (930).

FIG. 10 shows a perspective view of the card intermixing device (90) of the elements within the housing (800) (not shown). Four separate means to linearly translate an object (900) are shown: a means to linearly translate the first card-receiving structure (940), a means to linearly translate the card-edge lifting structure (910), a means to linearly translate the first push surface (920), and a means to linearly translate the second push surface (930).

Computer Controller (1000)

A computer controller (1000) is used to control the movements within the card intermixing device (90). Specifically, the means to linearly translate the first card-receiving structure (940), the means to linearly translate the card-edge lifting structure (910), the means to linearly translate the first push surface (920), and the means to linearly translate the second push surface (930) are operationally connected to the computer controller (1000). When the card intermixing device (90) further comprises the means to linearly translate the second card-receiving surface, this means to linearly translate the second card-receiving surface is operationally connected to the computer controller (1000).

An interface provides human interaction with the computer controller (1000). The interface is operatively connected with the computer controller (1000). The interface allows the setting of various operational variables for the use of the card intermixing device (90) such as: a. number of card decks being intermixed b. stack cutting parameters c. intermixing timeframe d. number of and parameters for intermixing cycles e. lifting member parameters f. automatic or on demand card stack entry/exit g. sanitizing off/on h. troubleshooting sequences Power Supply (1100)

The card intermixing device (90) comprises a power supply (1100). The input of the power supply (1100) may be AC power (e.g. wall plug), DC power (for stand-alone applications e.g. batteries) or both (with DC power as a back-up power source). The output of the power supply (1100) may be AC power, DC power, or both, depending on the power needs of the card intermixing device (90) elements. FIG. 13 shows the computer controller (1000) and the power supply (1100) at the bottom of the housing (800).

The DC power input embodiment is primarily utilized in spaces where card tables are deployed but AC power input is not available or impractical. This allows card intermixing at the card table in situations not otherwise possible—e.g. tables being temporarily set up for poker tournaments.

Operation of the Card Intermixing Device (90)

To start the card stack loading sequence, the first card-receiving surface (110) is vertically translated so that it can be accessed through the top aperture (810) of the top surface (820) or the side aperture (870) of the side surface (860), depending on the housing (800) embodiment being used. This allows the dealer to place the card stack (605) onto the first card-receiving surface (110). The first card-receiving surface (110) is translated by the means to linearly translate the first card-receiving surface (940).

If the card funnel (830) is present, the dealer places the card stack (605) into the card funnel (830) through the top opening (832) or the first side surface aperture (850) of the card funnel (830). When the dealer finishes placing the card stack (605) onto the first card-receiving surface (110), the first card-receiving surface (110) is vertically translated downwards. As the first card-receiving surface (110) is lowered, the cards (600) in the card stack (605) are "squared up" by the tapering of the side surfaces (840) of the card funnel (830). By the time the entire card stack (605) has been lowered through the first shape (812) of the top aperture (810), the card stack (605) is "squared up" and is ready to be intermixed.

To cut the card stack (605) into a first sub-stack (610) and a second sub-stack (620), the first push surface (300) is positioned in its initial first push surface position and the second push surface (400) is positioned in its initial second push surface position. The means to linearly translate the first card-receiving surface (940) translates vertically the first card-receiving surface (110) so that a portion of the card stack (605) is aligned below the bottom edge (310) of the first push surface (300) (the first sub-stack (610)) and a portion of the card stack (605) is aligned above the bottom edge (310) of the first push surface (300) (the second sub-stack (620)). When the first card-receiving surface (110) translates from the top aperture (810) of the housing (800), the first card-receiving surface (110) translates vertically downward. At this point, the first card-receiving surface (110) and the second card-receiving surface (210) are not necessarily flush. This "off-set" determines the height variation between the first sub-stack (610) and the second sub-stack (620) after being cut from the card stack (605). FIG. 13 shows a front sectional view of the housing (800), where the first card-receiving structure (100) has translated the card stack (605) so that a portion of the card stack (605) is aligned below the bottom edge (310) of the first push surface (300) (the first sub-stack (610)) and a portion of the card stack (605) is aligned above the bottom edge (310) of the first push surface (300) (the second sub-stack (620)).

The first push surface (300) then translates towards the second edge (114) of the first card-receiving surface (110), coming in contact with the portion of the card stack (605) aligned above the bottom edge (310) of the first push surface (300) (the second sub-stack (620)). The second sub-stack (620) is translated towards the second edge (214) of the second card-receiving surface (210) until it is positioned onto the second card-receiving surface (210). The second sub-stack (620) is now positioned adjacent to the first sub-stack (610). The second push surface (400) provides a stop point for the second sub-stack (620) and prevents further translation. The cards (600) in the card stack (605) below the bottom edge (310) of the first push surface (300) do not translate and remain over the first card-receiving surface (110)—the first sub-stack (610). FIG. 14 shows a front sectional view of the housing (800), where the first push surface (300) has translated the second sub-stack (620) onto the second card-receiving surface (210).

Once the second sub-stack (620) is positioned onto the second card-receiving surface (210), the first push surface (300) returns to its initial first push surface position. The first card-receiving surface (110) is vertically translated upwards until the first card-receiving surface (110) and the second card-receiving surface (210) are substantially flush. This also means that the bottom (616) of the first sub-stack (610) and the bottom (626) of the second sub-stack (620) are substantially flush. FIG. 15 shows a front sectional view of the housing (800), where the first card-receiving surface (110) is aligned to the second card-receiving surface (210) so that the first sub-stack (610) is adjacent to the second sub-stack (620).

The interleaving of the cards (600) of the first sub-stack (610) and the second sub-stack (620) begins by having the shaft (520) positioned below the first card-receiving surface (110) and the second card-receiving surface (210). The shaft (520) is translated upwards by the means to linearly translate the card-edge lifting structure (910). Once the shaft (520) comes into contact with the bottom (616) of the first sub-stack (610) and bottom (626) of the second sub-stack (620), the shaft (520) continues to translate upward, lifting the second edge (614) of the first sub-stack (610) and the first edge (622) of the second sub-stack (620). FIG. 16 shows a front sectional view of the housing (800), where the shaft (520) of the card-edge lifting structure (500) is being translated upwards, lifting the second edge (614) of the first sub-stack (610) and the first edge (622) of the second sub-stack (620).

As the shaft (520) translates upward, the first push surface (300) translates towards the second edge (114) of the first card-receiving surface (110) so that the first sub-stack (610) is pushed, and the second push surface (400) translates towards the first edge (212) of the second card-receiving surface (210) so that the second sub-stack (620) is pushed. These movements push the first sub-stack (610) and the second sub-stack (620) towards each other. These movements force the second edge (614) of the first sub-stack (610) and the first edge (622) of the second sub-stack (620) to interleave when the cards (600) from the first sub-stack (610) and the second sub-stack (620) fall. FIG. 16 shows the first push surface (300) translating towards the second edge (114) of the first card-receiving surface (110) so that the first sub-stack (610) is pushed, and the second push surface (400) translating towards the first edge (212) of the second card-receiving surface (210) so that the second sub-stack (620) is pushed.

When the shaft (520) reaches a certain height relative to the first card-receiving surface (110) and the second card-receiving surface (210), the edges of the cards (600) at the bottom (616) of the first sub-stack (610) and the bottom (626) of the second sub-stack (620) fall past the shaft (520).

As the cards (600) fall, the cards (600) from the first sub-stack (610) and the second sub-stack (620) interleave, creating an interleaved card stack (630). The shaft (520) continues to lift until all the cards (600) from the first sub-stack (610) and the second sub-stack (620) fall creating an interleaved card stack (630). This interleaving positions the cards (600) from the first sub-stack (610) and the second sub-stack (620) partly onto each other. It is necessary to "square up" the interleaved card stack (630) into the card stack (605) and to reposition the card stack (605). FIG. 17 shows a front sectional view of the housing (800), where the cards (600) from the bottom (616) of the first sub-stack (610) and cards (600) from the bottom (626) of the second sub-stack (620) have fallen past the shaft (520) and interleaved into an interleaved card stack (630). FIG. 18 shows an enlarged view of the interleaved card stack (630), where cards (600) from the first sub-stack (610) and cards (600)

from the second sub-stack (620) have been interleaved into an interleaved card stack (630).

As the cards (600) fall and the shaft (520) translates upward, the first push surface (300) may continue to translate towards the second edge (114) of the first card-receiving surface (110) and the second push surface (400) may continue to translate towards the first edge (212) of the second card-receiving surface (210). This translation maintains the second edge (614) of the first sub-stack (610) substantially flush against the card separator wall (510) and the first edge (622) of the second sub-stack (620) substantially flush against the card separator wall (510). This allows for a more controlled card falling process.

Once all the cards (600) from the first sub-stack (610) and the second sub-stack (620) have fallen and interleaved, creating an interleaved card stack (630), the cards (600) are "squared up" and repositioned in the card intermixing device (90) to continue the card intermixing process or to finish the card intermixing process. There are at least two methods to "square up" the cards (600) from the first sub-stack (610) and the second sub-stack (620) into the card stack (605) and to reposition the card stack (605) as described in the 2nd and 3rd Paragraph of SubSection Squaring Up and Repositioning.

Once the card stack (605) has been repositioned onto the first card-receiving surface (110), either a) the intermixing of the cards (600) is completed or b) the intermixing of the cards (600) continues and the card stack (605) goes through another intermixing cycle of the intermixing process.

When the intermixing of the cards (600) is completed, the card stack (605) is translated for removal from the housing (800). This translation may be automatic or on-demand. An on-demand option allows the card stack (605) to remain within the housing (800) after intermixing to eliminate the potential of the card stack (605) being hit and knocked over or being tampered. This on-demand option may be activated through the interface operatively connected to the computer controller (1000).

When the housing (800) comprises a top surface (820) and a top aperture (810), the first card-receiving surface (110) is translated vertically so that the card stack (605) can be accessed through the top aperture (810) of the top surface (820) of the housing (800). The card stack (605) emerges from the housing (800) and the dealer can remove the card stack (605) from the first card-receiving surface (110). If the second shape (814) of the top aperture (810) is present, the second shape (814) of the top aperture (810) and the finger notch (122) of the first card-receiving surface (110) allow the dealer to place a finger or a thumb under the card stack (605) for easier removal. If the card funnel (830) is present, the card stack (605) emerges through the top aperture (810) and the bottom opening (834) of the card funnel (830).

When the housing (800) comprises a side surface (860) and a side aperture (870), the first card-receiving surface (110) is translated vertically so that the card stack (605) can be accessed through the side aperture (870) of the side surface (860) of the housing (800).

If the intermixing of the cards (600) continues, the first card-receiving surface (110) is translated vertically by the means to linearly translate the first card-receiving surface (940) so that a portion of the card stack (605) is aligned below the bottom edge (310) of the first push surface (300). The intermixing process continues as described previously in the 13th Paragraph of SubSection Inside the Housing (800).

Clarifying Comments

While the foregoing written description of the invention enables a person having ordinary skill in the art to make and use what is considered presently to be the best mode thereof, those of ordinary skill in the art will understand and appreciate the existence of variations, combinations, and equivalents of the specific embodiment, process, and examples herein. The invention should therefore not be limited by the above described embodiment, process, and examples, but by all embodiments and processes within the scope and spirit of the invention.

The inventions shown and described herein may be used to address one or more of such problems or other problems not set out herein and/or which are only understood or appreciated at a later time. The future may also bring to light currently unknown or unrecognized benefits which may be appreciated, or more fully appreciated, in association with the inventions shown and described herein. The desires and expected benefits explained herein are not admissions that others have recognized such prior needs, since invention and discovery are both inventive under the law and may relate to the inventions described herein.

I claim:

1. A card intermixing device that intermixes cards of a card stack by cutting the card stack into a first sub-stack and a second sub-stack comprising:
    (a) a housing; the housing comprising: an aperture;
    (b) a first card-receiving structure, the first card-receiving structure comprising:
        (i) a first card-receiving surface, the first card-receiving surface comprising:
            (1) a first edge;
            (2) a second edge;
        (ii) a means to linearly translate the first card-receiving surface;
            (1) where the means to linearly translate the first card-receiving surface is connected to the first card-receiving surface,
            (2) where the means to linearly translate the first card-receiving surface translates vertically the card stack,
        (iii) where the first card-receiving surface can be accessed through the aperture of the housing, and the card stack can be placed onto the first card-receiving surface,
    (c) a second card-receiving structure, the second card-receiving structure comprising:
        (i) a second card-receiving surface, the second card-receiving surface comprising:
            (1) a first edge;
            (2) a second edge;
    (d) a first push surface; where the first push surface translates cards from the card stack,
    (e) a means to linearly translate the first push surface; where the means to linearly translate the first push surface is connected to the first push surface,
    (f) a second push surface; where the second push surface translates cards from the card stack,
    (g) a means to linearly translate the second push surface; where the means to linearly translate the second push surface is connected to the second push surface,
    (h) one or more card-edge lifting structures, each card-edge lifting structure comprising:

(i) a shaft;
(ii) a card separator wall;
(iii) a means to linearly translate the shaft;
(iv) where the shaft is pivotally connected to the means to linearly translate the shaft,
(v) where the shaft vertically translates either a second edge of the first sub-stack, a first edge of the second sub-stack or both,
(i) a gap;
(i) where the gap is located between the second edge of the first card-receiving surface and the first edge of the second card-receiving surface,
(ii) where each card-edge lifting structure vertically translates within the gap.

2. The card intermixing device described in claim 1,
(a) wherein the housing further comprises: a top surface;
(b) where the aperture is located on the top surface
(c) where the card stack is placed on the first card-receiving surface through the aperture in the top surface.

3. The card intermixing device described in claim 2,
(a) wherein the housing further comprises a card funnel, the card funnel comprising:
(i) a top opening;
(ii) a bottom opening;
(iii) a first side surface;
(iv) a second side surface;
(v) a third side surface;
(vi) an aperture;
(vii) where the card stack can be placed into the card funnel through the top opening and the aperture of the card funnel,
(b) where the card funnel has a pyramid frustrum shape,
(c) where the bottom opening of the card funnel is aligned with the aperture of the top surface of the housing.

4. The card intermixing device described in claim 3,
(a) wherein the card funnel further comprises:
(i) a fourth side surface, the fourth side surface comprising a notch;
(ii) where the fourth side surface is coplanar to the aperture of the card funnel.

5. The card intermixing device described in claim 3,
(a) wherein the first card-receiving surface further comprises:
(i) a channel;
(b) where the channel is oriented from the first edge of the first card-receiving surface to the second edge of the first card-receiving surface.

6. The card intermixing device described in claim 3,
(a) wherein the shaft has a triangular prism shape.

7. The card intermixing device described in claim 3,
(a) wherein the shaft has an asymmetrical cross section with reference to the card separator wall.

8. The card intermixing device described in claim 3,
(a) wherein the shaft has a symmetrical cross section with reference to the card separator wall.

9. The card intermixing device described in claim 3 further comprising:
(a) a means to sanitize cards.

10. The card intermixing device described in claim 3:
(a) further comprising a first push surface vibration actuator and a second push surface vibration actuator;
(i) where the first push surface vibration actuator is operatively connected to the first push surface;
(ii) where the second push surface vibration actuator is operatively connected to the second push surface,
(b) wherein each card-edge lifting structure further comprises a card-edge vibration actuator;
(i) where the card-edge vibration actuator is operatively connected to the shaft.

11. The card intermixing device described in claim 1,
(a) wherein the housing further comprises a side surface;
(b) where the aperture is located on the side surface;
(c) where the card stack is placed on the first card-receiving surface through the aperture in the side surface.

12. The card intermixing device described in claim 1,
(a) wherein the second card-receiving structure further comprises a means to linearly translate the second card-receiving surface;
(i) where the means to linearly translate the second card-receiving surface translates vertically.

* * * * *